United States Patent
Shin et al.

(10) Patent No.: US 10,919,992 B2
(45) Date of Patent: Feb. 16, 2021

(54) INDENE-BASED TRANSITION METAL COMPOUND, TRANSITION METAL CATALYST COMPOSITION COMPRISING SAME, AND METHOD FOR PREPARING ETHYLENE HOMOPOLYMER OR COPOLYMER OF ETHYLENE AND ALPHA-OLEFIN BY USING SAME

(71) Applicant: SABIC SK NEXLENE COMPANY PTE. LTD., Singapore (SG)

(72) Inventors: Dong-cheol Shin, Daejeon (KR); Yeonock Oh, Anyang-Si (KR)

(73) Assignee: SABIC SK NEXLENE COMPANY PTE. LTD., Singapore (SG)

( * ) Notice: Subject to any disclaimer, the term of this patent is extended or adjusted under 35 U.S.C. 154(b) by 0 days.

(21) Appl. No.: 16/650,848

(22) PCT Filed: Sep. 28, 2018

(86) PCT No.: PCT/IB2018/057534
§ 371 (c)(1),
(2) Date: Mar. 25, 2020

(87) PCT Pub. No.: WO2019/064247
PCT Pub. Date: Apr. 4, 2019

(65) Prior Publication Data
US 2020/0262943 A1    Aug. 20, 2020

(30) Foreign Application Priority Data

Sep. 29, 2017 (KR) .................. 10-2017-0127528
Sep. 27, 2018 (KR) .................. 10-2018-0115040

(51) Int. Cl.
   *C07F 7/28*        (2006.01)
   *C07F 7/08*        (2006.01)
               (Continued)

(52) U.S. Cl.
   CPC ......... *C08F 4/6592* (2013.01); *B01J 31/1608* (2013.01); *B01J 31/1805* (2013.01);
               (Continued)

(58) Field of Classification Search
None
See application file for complete search history.

(56) References Cited

U.S. PATENT DOCUMENTS 6,555,634 B1 * 4/2003 Klosin ................ C07F 17/00
                                         502/103

FOREIGN PATENT DOCUMENTS

EP       0320762 A2    6/1989
EP       0372632 A1    6/1990
               (Continued)

OTHER PUBLICATIONS

Reb, A. et al., "Diastereonneric amido functionalized ansa half-sandwich complexes of titanium and zirconium as catalyst precursors for ethylene polymerization to give resins with bimodal molecular weight distributions". Journal of Molecular Catalysis A: Chemical 2001, 174, 35-49. (Year: 2001).*

(Continued)

*Primary Examiner* — Richard A Huhn
(74) *Attorney, Agent, or Firm* — McCoy Russell LLP

(57) ABSTRACT

Provided are a novel indene-based transition metal complex, a transition metal catalyst composition including the same having high catalyst activity for preparing an ethylene homopolymer or copolymers of ethylene and one or more α-olefins, a method for preparing an ethylene homopolymer or copolymers of ethylene and α-olefins using the same, and the thus-prepared ethylene homopolymer or copolymers of ethylene and α-olefins.

18 Claims, 2 Drawing Sheets

(51) Int. Cl.
*C07F 7/10* (2006.01)
*C07C 13/465* (2006.01)
*C07C 291/00* (2006.01)
*B01J 31/16* (2006.01)
*B01J 31/18* (2006.01)
*C08F 10/02* (2006.01)
*C08F 4/6592* (2006.01)
*C08F 4/646* (2006.01)
*C08F 210/02* (2006.01)
*C08F 210/06* (2006.01)
*C08F 110/02* (2006.01)

(52) U.S. Cl.
CPC .......... *C07C 13/465* (2013.01); *C07C 291/00* (2013.01); *C07F 7/08* (2013.01); *C07F 7/0803* (2013.01); *C07F 7/10* (2013.01); *C07F 7/28* (2013.01); *C08F 4/646* (2013.01); *C08F 10/02* (2013.01); *C08F 110/02* (2013.01); *C08F 210/02* (2013.01); *C08F 210/06* (2013.01); *C07C 2531/14* (2013.01); *C07C 2531/18* (2013.01); *C07C 2531/38* (2013.01); *C08F 2500/05* (2013.01)

(56) References Cited

FOREIGN PATENT DOCUMENTS

| | | |
|---|---|---|
| EP | 0416815 A2 | 3/1991 |
| EP | 0417302 A1 | 3/1991 |
| EP | 0420436 A1 | 4/1991 |
| EP | 0842939 A1 | 5/1998 |
| JP | S6392621 A | 4/1988 |
| JP | H0284405 A | 3/1990 |
| JP | H032347 A | 1/1991 |
| KR | 20000029833 A | 5/2000 |
| KR | 20040083922 A | 10/2004 |
| KR | 20050112135 A | 11/2005 |
| KR | 101002620 B1 | 12/2010 |

OTHER PUBLICATIONS

Reb, A. et al., "Diastereomeric amido functionalized ansa half-sandwich complexes of titanium and zirconium as catalyst precursors for ethylene polymerization to give resins with bimodal molecular weight distributions," Journal of Molecular Catalysis A: Chemical, vol. 174, No. 1-2, Oct. 1, 2001, 15 pages.
ISA Korean Intellectual Property Office, International Search Report Issued in Application No. PCT/IB2018/057534, Jan. 29, 2019, WIPO, 6 pages.

* cited by examiner

INDENE-BASED TRANSITION METAL COMPOUND, TRANSITION METAL CATALYST COMPOSITION COMPRISING SAME, AND METHOD FOR PREPARING ETHYLENE HOMOPOLYMER OR COPOLYMER OF ETHYLENE AND ALPHA-OLEFIN BY USING SAME

CROSS-REFERENCE TO RELATED APPLICATIONS

The present application is a U.S. National Phase of International Patent Application Serial No. PCT/IB2018/057534 entitled "NOVEL INDENE-BASED TRANSITION METAL COMPOUND, TRANSITION METAL CATALYST COMPOSITION COMPRISING SAME, AND METHOD FOR PREPARING ETHYLENE HOMOPOLYMER OR COPOLYMER OF ETHYLENE AND α-OLEFIN BY USING SAME," filed on Sep. 28, 2018. International Patent Application Serial No. PCT/IB2018/057534 claims priority to Korean Patent Application No. 10-2017-0127528 filed on Sep. 29, 2017 and Korean Patent Application No. 10-2018-0115040 filed on Sep. 27, 2018. The entire contents of each of the above-referenced applications are hereby incorporated by reference for all purposes.

TECHNICAL FIELD

The following disclosure relates to a novel indene-based transition metal complex, a transition metal catalyst composition including the same having high catalyst activity for preparing an ethylene homopolymer or copolymers of ethylene and one or more α-olefins, a method for preparing an ethylene homopolymer or copolymers of ethylene and α-olefins using the same, and the thus-prepared ethylene homopolymer or copolymers of ethylene and α-olefins.

BACKGROUND

Conventionally, in the preparation of a homopolymer of ethylene or copolymers of ethylene and α-olefins, so called, a Ziegler-Natta catalyst system including a main catalyst component of a titanium or vanadium compound, and a cocatalyst component of an alkyl aluminum compound has been used. However, though the Ziegler-Natta catalyst system represents high activity to ethylene polymerization, it has a demerit in that generally a produced polymer has a broad molecular weight distribution due to an active heterogeneous catalytic site, and in particular copolymers of ethylene and α-olefins have a non-uniform composition distribution.

Recently, so called, a metallocene catalyst system including a metallocene compound of Group 4 transition metals in the periodic table such as titanium, zirconium and hafnium and methylaluminoxane as a cocatalyst has been developed. Since the metallocene catalyst system is a homogeneous catalyst having a single catalyst active site, it is characterized by preparing polyethylene having a narrow molecular weight distribution and a uniform composition distribution as compared with the conventional Ziegler-Natta catalyst system. For example, European Patent Application Publication Nos. 320,762 and 372,632, or Japanese Patent Laid-Open Publication Nos. (Sho) 63-092621, (Hei) 02-84405, or (Hei) 03-2347 disclose that a metallocene compound is activated with cocatalyst methyl aluminoxane in $Cp_2TiCl_2$, $Cp_2ZrCl_2$, $Cp_2ZrMeCl$, $Cp_2ZrMe_2$, ethylene$(IndH_4)_2ZrCl_2$ and the like to polymerize ethylene with high activity, thereby preparing polyethylene having a molecular weight distribution (Mw/Mn) in a range of 1.5-2.0. However, it is difficult to obtain a high molecular weight polymer with the catalyst system, and in particular, when the catalyst system is applied to a solution polymerization method carried out at a high temperature of 100° C. or more, polymerization activity is rapidly decreased, and a β-dehydrogenation reaction is predominant, and thus, the catalyst system is not suitable for preparing a high molecular weight polymer having a weight average molecular weight (Mw) of 100,000 or more.

Meanwhile, as a catalyst capable of preparing a high molecular weight polymer with high catalyst activity in an ethylene homopolymer or copolymers of ethylene and α-olefins under a solution polymerization condition, so called, a constrained geometric non-metallocene-based catalyst (also known as a single active site catalyst) having a transition metal connected in the form of a ring has been published. European Patent Publication Nos. 0416815 and 0420436 suggest an example in which an amide group is linked to one cyclopentadiene ligand in the form of a ring, and European Patent Publication No. 0842939 shows an example of a catalyst which links a phenol-based ligand to a cyclopentadiene ligand in the form of a ring, as an electron donating compound. Though this constrained geometric catalyst has significantly improved reactivity with higher α-olefins due to the lowered steric hindrance effect of the catalyst itself, it is commercially important to develop a catalyst which provides excellent activity, an excellent copolymerization property, and the like at high temperature.

Meanwhile, according to a conventional literature, "Journal of Molecular Catalysis A: Chemical 174 (2001) 35-49", in the case of an indene-based catalyst in which both aryl group and alkyl group are substituted in a silyl linking group, diastereomers are prepared, which showed a characteristic representing a broad molecular weight distribution. Therefore, the proportions of the diastereomers may be different for each prepared catalyst, and the different proportions of the diastereomers cause inconsistency such as a varied molecular weight distribution of the final product, and thus, the indene-based catalyst is difficult to be commercially applied.

SUMMARY

Technical Problem

In order to overcome the above problems of the prior art, the present inventors conducted an extensive study, and as a result, found that a transition metal complex having a structure in which a Group 4 transition metal in the periodic table is linked by an indene or a derivative group thereof having a rigid plane structure with abundant and widely delocalized electrons and a nitrogen-containing substituent introduced thereto; and an amido group having a substituted silyl group, while in particular, having a structural characteristic including both an alkyl group or alkenyl group and an aryl group in a silyl group linking the indene or the derivative group having a nitrogen-containing substituent introduced thereto and the amido group, has merits such as excellent activity at high temperature in polymerization of ethylene and olefins, and excellent solubility in a solvent such as normal hexane and cyclohexane, and also, found that the catalysts developed in the present invention have characteristics such as producing a high molecule having a narrow molecular weight distribution despite the presence of diastereomers, and representing high activity even at high temperature, thereby completing the present invention.

An embodiment of the present invention is directed to providing a transition metal complex useful as a catalyst for preparing an ethylene homopolymer or copolymers of ethylene and α-olefins, and also a catalyst composition including the same.

Another embodiment of the present invention is directed to providing a method for preparing an ethylene homopolymer or copolymers of ethylene and α-olefins economically from a commercial point of view, using a catalyst composition including the transition metal complex.

Another embodiment of the present invention is directed to providing a transition metal complex for use in preparing copolymers of ethylene and α-olefins having a unimodal GPC graph.

Still another embodiment of the present invention is directed to providing a method for preparing copolymers of ethylene and α-olefins having a chemical composition distribution represented by a unimodal or bimodal graph, using the transition metal complex.

Technical Solution

In one general aspect, an indene-based transition metal complex is represented by the following Chemical Formula 1. More specifically, the transition metal complex has a structure in which a Group 4 transition metal in the periodic table as a center metal is linked by an indene or a derivative group thereof having a rigid plane structure with abundant and widely delocalized electrons and a nitrogen-containing substituent introduced thereto; and an amido group having a substituted silyl group, while in particular, having a structural characteristic including both an alkyl group or alkenyl group and an aryl group in a silyl group linking the indene or the derivative group having a nitrogen-containing substituent introduced thereto and the amido group.

Chemical Formula 1

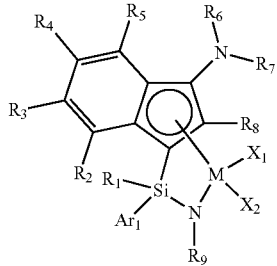

wherein
M is a Group 4 transition metal in the periodic table;
$R_1$ is (C1-C20)alkyl or (C2-C20)alkenyl, in which the alkyl or alkenyl of $R_1$ may be further substituted by one or more substituents selected from the group consisting of halogen, (C6-C30)aryl and (C1-C20)alkyl(C6-C30)aryl;
$Ar_1$ is (C6-C30)aryl, in which the aryl of $Ar_1$ may be further substituted by one or more substituents selected from the group consisting of (C1-C20)alkyl, halo(C1-C20)alkyl and (C6-C30)aryl(C1-C20)alkyl;
$R_2$ to $R_5$ are each independently hydrogen, (C1-C20) alkyl, (C1-C20)alkoxy, halo(C1-C20)alkyl, (C3-C20) cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl or ((C1-C20)alkyl(C6-C30)aryl)(C1-C20)alkyl, or $R_2$ to $R_5$ may be linked with an adjacent substituent to form a fused ring, in which the formed fused ring may be further substituted by one or more substituents selected from the group consisting of (C1-C20)alkyl, (C1-C20)alkoxy, halo (C1-C20)alkyl, (C3-C20)cycloalkyl, (C1-C20)alkyl (C6-C30)aryl, (C6-C30)aryl, (C6-C30)aryloxy, (C1-C20)alkyl(C6-C30)aryloxy, (C6-C30)aryl(C1-C20) alkyl and ((C1-C20)alkyl(C6-C30)aryl)(C1-C20)alkyl;

$R_9$ is (C1-C20)alkyl, (C3-C20)cycloalkyl or (C6-C30)aryl (C1-C20)alkyl;

$R_6$ and $R_7$ are each independently (C1-C20)alkyl, halo (C1-C20)alkyl, (C3-C20)cycloalkyl, (C6-C30)aryl, (C1-C20)alkyl(C6-C30)aryl, (C1-C20)alkoxy(C6-C30)aryl or (C6-C30)aryl(C1-C20)alkyl, or $R_6$ and $R_7$ may be linked to each other to form a ring, in which the formed ring may be further substituted by one or more substituents selected from the group consisting of (C1-C20)alkyl, halo(C1-C20)alkyl, (C6-C30)aryl(C1-C20) alkyl, (C1-C20)alkoxy, (C3-C20)cycloalkyl, (C6-C20) aryl, (C1-C20)alkyl(C6-C30)aryl and (C6-C20) aryloxy;

$R_8$ is hydrogen or (C1-C20)alkyl;

$X_1$ and $X_2$ are each independently halogen, (C1-C20) alkyl, (C2-C20)alkenyl, (C3-C20)cycloalkyl, (C6-C30) aryl, (C6-C30)ar(C1-C20)alkyl, ((C1-C20)alkyl(C6-C30)aryl)(C1-C20)alkyl, (C1-C20)alkoxy, (C6-C30) aryloxy, (C1-C20)alkyl(C6-C30)aryloxy, (C1-C20) alkoxy(C6-C30)aryloxy, —OSi$R^a R^b R^c$, —S$R^d$, —N$R^e R^f$, —P$R^g R^h$ or (C1-C20)alkylidene;

$R^a$ to $R^d$ are each independently (C1-C20)alkyl, (C6-C20) aryl, (C6-C20)ar(C1-C20)alkyl, (C1-C20)alkyl(C6-C20)aryl or (C3-C20)cycloalkyl; and $R^e$ to $R^h$ are each independently (C1-C20)alkyl, (C6-C20) aryl, (C6-C20)ar(C1-C20)alkyl, (C1-C20)alkyl(C6-C20)aryl, (C3-C20)cycloalkyl, tri(C1-C20)alkylsilyl or tri(C6-C20)arylsilyl;

with a proviso that when one of $X_1$ and $X_2$ is (C1-C20) alkylidene, the other one is ignored.

In another general aspect, a transition metal catalyst composition for preparing an ethylene homopolymer or copolymers of ethylene and α-olefins includes the transition metal complex of Chemical Formula 1; and a cocatalyst selected from the group consisting of an aluminum compound, a boron compound and a mixture thereof.

In another general aspect, a method for preparing an ethylene homopolymer or copolymers of ethylene and α-olefins using the transition metal catalyst composition is provided.

In another general aspect, a method for preparing copolymers of ethylene, α-olefins and dienes using the transition metal complex or a catalyst composition including the transition metal complex is provided.

In another general aspect, a compound represented by Formula Int-1 as an intermediate for preparing the transition metal complex of Chemical Formula 1 is provided:

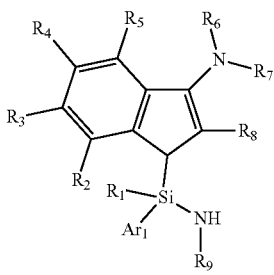

Chemical Formula Int-1 wherein $R_1$ to $R_9$ and $Ar_1$ are as defined in the above Chemical Formula 1.

In another general aspect, a transition metal complex for use in preparing copolymers of ethylene and α-olefins having a unimodal GPC graph is provided.

In another general aspect, a method for preparing copolymers of ethylene and α-olefins having a chemical composition distribution represented by a unimodal or bimodal graph, using the transition metal complex.

Advantageous Effects

The transition metal complex according to the present invention or the catalyst composition including the transition metal complex has a high synthesis yield, may be easily prepared by an economical method, and also has excellent catalyst thermal stability to maintain high catalyst activity even at high temperature while having good copolymerization reactivity with other olefins, and may produce a high molecular weight polymer with a high yield, and thus, has high commercial practicality as compared with already known metallocene and non-metallocene-based single active site catalysts. The present inventors have developed catalysts which are diastereomer catalysts, but show a narrow molecular weight distribution characteristic like a single activity site catalyst, by controlling the ligands. That is, the copolymer prepared using the transition metal complex according to the present invention as a catalyst having high activity at high temperature has unique merits in that copolymers having a narrow molecular weight distribution and a narrow chemical composition distribution (CCD) may be easily prepared, and a product having a narrow molecular weight distribution and a broad chemical composition distribution (2 peaks) may be also prepared. Therefore, the transition metal catalyst composition according to the present invention may be useful for preparing an ethylene-based polymer selected from copolymers of ethylene and α-olefins having various physical properties.

DETAILED DESCRIPTION

Figure 1:
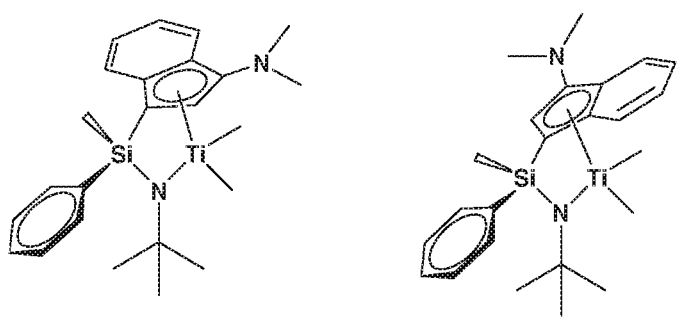
FIG. 1 represents two isomers of Complex 1.

Hereinafter, the present invention will be described in more detail. Technical terms and scientific terms used in the present specification have the general meaning understood by those skilled in the art to which the present invention pertains unless otherwise defined, and a description for the known function and configuration obscuring the present invention will be omitted in the following description.

The transition metal complex according to an exemplary embodiment of the present invention is a transition metal complex based on an indenyl group having a nitrogen-containing substituent introduced thereto, represented by the following Chemical Formula 1, and has a structure in which a Group 4 transition metal in the periodic table as a center metal is linked by an indene or the derivative group thereof having a rigid plane structure with abundant and widely delocalized electrons and a nitrogen-containing substituent introduced thereto; and an amido group having a substituted silyl group, while in particular, having a structural characteristic including both an alkyl group or alkenyl group and an aryl group which induce improved solubility in a general hydrocarbon solvent, greatly increased activity at high temperature, and a narrow molecular weight distribution, not a broad molecular weight distribution which is a deficiency of diastereomers, in the silyl group linking the indene or the derivative group having a nitrogen-containing substituent introduced thereto and the amido group, and thus, has a structural merit of being advantageous to obtain a high molecular weight ethylene-based polymer at high temperature with high efficiency.

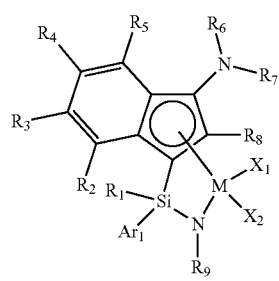

Chemical Formula 1 wherein
M is a Group 4 transition metal in the periodic table;
$R_1$ is (C1-C20)alkyl or (C2-C20)alkenyl, in which the alkyl or alkenyl of $R_1$ may be further substituted by one or more substituents selected from the group consisting of halogen, (C6-C30)aryl and (C1-C20)alkyl(C6-C30)aryl;

Ar$_1$ is (C6-C30)aryl, in which the aryl of Ar$_1$ may be further substituted by one or more substituents selected from the group consisting of (C1-C20)alkyl, halo(C1-C20)alkyl and (C6-C30)aryl(C1-C20)alkyl;

R$_2$ to R$_5$ are each independently hydrogen, (C1-C20) alkyl, (C1-C20)alkoxy, halo(C1-C20)alkyl, (C3-C20) cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl or ((C1-C20)alkyl(C6-C30)aryl)(C1-C20)alkyl, or R$_2$ to R$_5$ may be linked with an adjacent substituent to form a fused ring, in which the formed fused ring may be further substituted by one or more substituents selected from the group consisting of (C1-C20)alkyl, (C1-C20)alkoxy, halo (C1-C20)alkyl, (C3-C20)cycloalkyl, (C1-C20)alkyl (C6-C30)aryl, (C6-C30)aryl, (C6-C30)aryloxy, (C1-C20)alkyl(C6-C30)aryloxy, (C6-C30)aryl(C1-C20) alkyl and ((C1-C20)alkyl(C6-C30)aryl)(C1-C20)alkyl;

R$_9$ is (C1-C20)alkyl, (C3-C20)cycloalkyl or (C6-C30)aryl (C1-C20)alkyl;

R$_6$ and R$_7$ are each independently (C1-C20)alkyl, halo (C1-C20)alkyl, (C3-C20)cycloalkyl, (C6-C30)aryl, (C1-C20)alkyl(C6-C30)aryl, (C1-C20)alkoxy(C6-C30)aryl or (C6-C30)aryl(C1-C20)alkyl, or R$_6$ and R$_7$ may be linked to each other to form a ring, in which the formed ring may be further substituted by one or more substituents selected from the group consisting of (C1-C20)alkyl, halo(C1-C20)alkyl, (C6-C30)aryl(C1-C20) alkyl, (C1-C20)alkoxy, (C3-C20)cycloalkyl, (C6-C20) aryl, (C1-C20)alkyl(C6-C30)aryl and (C6-C20) aryloxy;

R$_8$ is hydrogen or (C1-C20)alkyl;

X$_1$ and X$_2$ are each independently halogen, (C1-C20) alkyl, (C2-C20)alkenyl, (C3-C20)cycloalkyl, (C6-C30) aryl, (C6-C30)ar(C1-C20)alkyl, ((C1-C20)alkyl(C6-C30)aryl)(C1-C20)alkyl, (C1-C20)alkoxy, (C6-C30) aryloxy, (C1-C20)alkyl(C6-C30)aryloxy, (C1-C20) alkoxy(C6-C30)aryloxy, —OSiR$^a$R$^b$R$^c$, —SR$^d$, —NR$^e$R$^f$, —PR$^g$R$^h$ or (C1-C20)alkylidene;

R$^a$ to R$^d$ are each independently (C1-C20)alkyl, (C6-C20) aryl, (C6-C20)ar(C1-C20)alkyl, (C1-C20)alkyl(C6-C20)aryl or (C3-C20)cycloalkyl; and R$^e$ to R$^h$ are each independently (C1-C20)alkyl, (C6-C20) aryl, (C6-C20)ar(C1-C20)alkyl, (C1-C20)alkyl(C6-C20)aryl, (C3-C20)cycloalkyl, tri(C1-C20)alkylsilyl or tri(C6-C20)arylsilyl;

with a proviso that when one of X$_1$ and X$_2$ is (C1-C20) alkylidene, the other one is ignored.

The transition metal complex of the present invention is a catalyst having a structural characteristic including both the alkyl group or alkenyl group and the aryl group in the silyl group linking the indenyl group having a nitrogen-containing substituent introduced thereto and the amido group, and thus, has a structural characteristic having both the merit of the alkyl group or alkenyl group which is advantageous in terms of activity and solubility, and the merit of the aryl group having a good injection property of a higher α-olefin. In addition, due to the structural characteristic including both the alkyl group or alkenyl group and the aryl group in the silyl group, it was confirmed by $^1$H-NMR that two types of diastereomers are present, as shown in FIG. 1. The catalysts developed in the present invention represent characteristics such as producing high molecules having a narrow molecular weight distribution despite the presence of diastereomers at a ratio of 1:1 to 1:8, and representing high activity even at high temperature. Conventionally, it has been previously reported that the catalysts having diastereomers having an indenyl group and an amido group linked by a silyl group have a characteristic of a broad molecular weight distribution. However, the catalysts developed in the present invention may produce a polymer having a narrow molecular weight distribution at high temperature with a high yield. In particular, the catalysts may have a great commercial value, since a polymer having a characteristic of a narrow molecular weight distribution and a narrow composition distribution may be obtained, and a polymer having a characteristic of a narrow molecular weight distribution and a broad chemical composition distribution may be obtained, by adjusting the substituents.

The term described herein, 'alkyl' refers to a monovalent straight-chain or branched-chain saturated hydrocarbon radical consisting of only carbon and hydrogen atoms, and an example of the alkyl radical includes methyl, ethyl, propyl, isopropyl, butyl, isobutyl, t-butyl, pentyl, hexyl, octyl, nonyl, or the like, but not limited thereto.

The term described herein, 'aryl' refers to an organic radical derived from aromatic hydrocarbon by removal of one hydrogen, including a monocyclic or fused ring system containing suitably 4 to 7, preferably 5 or 6 ring atoms in each ring, and even a form in which a plurality of aryls is linked by a single bond. A fused ring system may include an aliphatic ring such as saturated or partially saturated rings, and necessarily includes one or more aromatic rings. In addition, the aliphatic ring may contain nitrogen, oxygen, sulfur, carbonyl and the like in the ring. The specific example of the aryl radical includes phenyl, naphthyl, biphenyl, indenyl, fluorenyl, phenanthrenyl, anthracenyl, triphenylenyl, pyrenyl, chrysenyl, naphthacenyl, 9,10-dihydroanthracenyl and the like.

The term described herein, "cycloalkyl" refers to a monovalent saturated carbocyclic radical composed of one or more rings. An example of the cycloalkyl radical includes cyclopropyl, cyclobutyl, cyclopentyl, cyclohexyl, cycloheptyl, or the like, but not limited thereto.

The term described herein, "halo" or "halogen" refers to fluorine, chlorine, bromine or iodine atom.

The term described herein, "haloalkyl" refers to alkyl substituted by one or more halogens, and an example thereof may include trifluoromethyl, or the like.

The terms described herein, "alkoxy" and "aryloxy" refer to an —O-alkyl radical and an —O-aryl radical, respectively, wherein 'alkyl' and 'aryl' are as defined above.

In an exemplary embodiment of the present invention, the transition metal complex of the above Chemical Formula 1 may be a transition metal complex represented by the following Chemical Formula 2:

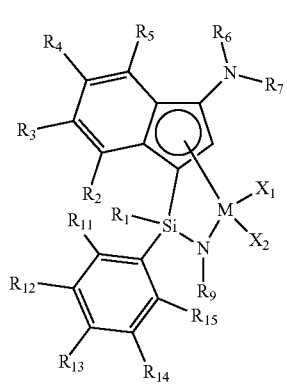

Chemical Formula 2 wherein M, $R_1$, $R_6$, $R_7$, $R_9$, $X_1$ and $X_2$ are as defined in the above Chemical Formula 1;

$R_2$ to $R_5$ are each independently hydrogen, (C1-C20)alkyl, (C1-C20)alkoxy, halo(C1-C20)alkyl, (C3-C20)cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl or ((C1-C20)alkyl(C6-C30)aryl)(C1-C20)alkyl, or $R_2$ to $R_5$ may be linked with an adjacent substituent by (C3-C7)alkylene, (C3-C7)alkenylene or (C4-C7)alkadienylene containing or not containing an aromatic ring to form a fused ring, in which the formed fused ring may be further substituted by one or more substituents selected from the group consisting of (C1-C20)alkyl, (C1-C20)alkoxy, halo(C1-C20)alkyl, (C3-C20)cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl and ((C1-C20)alkyl(C6-C30)aryl)(C1-C20)alkyl; and $R_{11}$ to $R_{15}$ are each independently hydrogen, (C1-C20)alkyl, halo(C1-C20)alkyl or (C6-C30)aryl(C1-C20)alkyl.

In an exemplary embodiment of the present invention, M of the transition metal complex is a Group 4 transition metal in the periodic table, and may be preferably titanium (Ti), zirconium (Zr) or hafnium (Hf), and more preferably titanium (Ti) or zirconium (Zr).

The (C1-C20)alkyl group is, for example, a methyl group, an ethyl group, an n-propyl group, an isopropyl group, an n-butyl group, an isobutyl group, a sec-butyl group, a tert-butyl group, an n-pentyl group, a neopentyl group, an amyl group, an n-hexyl group, an n-octyl group, an n-decyl group, an n-dodecyl group or an n-pentadecyl group; the (C2-C20)alkenyl group is, for example, a vinyl group or an allyl group; the (C3-C20)cycloalkyl group is, for example, a cyclopropyl group, a cyclobutyl group, a cyclopentyl group, a cyclohexyl group, a cycloheptyl group, a cyclooctyl group, a cyclodecyl group or a cyclododecyl group; the (C6-C30)aryl group or (C1-C20)alkyl(C6-C30)aryl group is, for example, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl(biphenyl) group, a fluorenyl group, a triphenyl group, a naphthyl group or anthracenyl group; the (C6-C30)aryl(C1-C10)alkyl group or the ((C1-C20)alkyl(C6-C30)aryl)(C1-C20)alkyl group is, for example, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethyl-phenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, (n-octylphenyl)methyl group, a (n-decylphenyl)methyl group, a (n-tetradecylphenyl)methyl group, a naphthylmethyl group or an anthracenylmethyl group; the (C1-C20)alkoxy group is, for example, a methoxy group, an ethoxy group, an n-propoxy group, an isopropoxy group, an n-butoxy group, a sec-butoxy group, a tert-butoxy group, an n-pentoxy group, a neopentoxy group, an n-hexoxy group, an n-octoxy group, an n-dodexoxy group, an n-pentadexoxy group or n-eicoxoxy group.

In an exemplary embodiment of the present invention, in the above Chemical Formula 2, $R_6$ and $R_7$ may be each independently (C1-C20)alkyl, (C3-C20)cycloalkyl or (C6-C30)aryl, or $R_6$ and $R_7$ may be linked by (C3-C7)alkylene containing or not containing an aromatic ring to form a ring, in which the formed ring may be further substituted by one or more substituents selected from the group consisting of (C1-C20)alkyl, (C6-C30)aryl(C1-C20)alkyl, (C1-C20)alkoxy, (C3-C20)cycloalkyl, (C6-C20)aryl, (C1-C20)alkyl(C6-C30)aryl and (C6-C20)aryloxy.

In an exemplary embodiment of the present invention, $R_1$ may be (C1-C20)alkyl, (C2-C20)alkenyl or (C6-C30)aryl(C1-C20)alkyl; $Ar_1$ may be (C6-C30)aryl or (C1-C20)alkyl(C6-C30)aryl; $R_2$ to $R_5$ may be each independently hydrogen, (C1-C20)alkyl, (C1-C20)alkoxy, (C1-C20)alkyl(C6-C30)aryl, (C6-C30)aryl, (C6-C30)aryloxy, (C1-C20)alkyl(C6-C30)aryloxy or (C6-C30)aryl(C1-C20)alkyl, or $R_2$ to $R_5$ may be linked with an adjacent substituent by (C3-C7)alkylene, (C3-C7)alkenylene or (C4-C7)alkadienylene containing or not containing an aromatic ring to form a fused ring, in which the formed fused ring may be further substituted by one or more substituents selected from the group consisting of (C1-C20)alkyl, (C1-C20)alkyl(C6-C30)aryl, (C6-C30)aryl, (C6-C30)aryl(C1-C20)alkyl and ((C1-C20)alkyl(C6-C30)aryl)(C1-C20)alkyl; $R_9$ is (C1-C20)alkyl, (C3-C20)cycloalkyl or (C6-C30)aryl(C1-C20)alkyl; $R_6$ and $R_7$ are each independently (C1-C20)alkyl, (C3-C20)cycloalkyl, (C6-C30)aryl, (C1-C20)alkyl(C6-C30)aryl, (C1-C20)alkoxy(C6-C30)aryl or (C6-C30)aryl(C1-C20)alkyl, or $R_6$ and $R_7$ may be linked by (C3-C7)alkylene containing or not containing an aromatic ring to form a ring, in which the formed ring may be further substituted by one or more substituents selected from the group consisting of (C1-C20)alkyl, (C6-C30)aryl(C1-C20)alkyl, (C1-C20)alkoxy, (C3-C20)cycloalkyl, (C6-C20)aryl, (C1-C20)alkyl(C6-C30)aryl and (C6-C20)aryloxy; and $R_8$ may be hydrogen or (C1-C20)alkyl.

In an exemplary embodiment of the present invention, $R_1$ may be more specifically a methyl group, an ethyl group, an n-propyl group, an isopropyl group, an n-butyl group, a vinyl group, an allyl group or a benzyl group; $Ar_1$ may be more specifically a phenyl group, a naphthyl group, a biphenyl group, a tolyl group, a trimethylphenyl group, a butylphenyl group, a pentylphenyl group, a hexylphenyl group, an octylphenyl group, a decylphenyl group, a dodecylphenyl group or a tetradecylphenyl group; $R_2$ to $R_5$ may be each independently hydrogen, a methyl group, an ethyl group, an n-propyl group, an isopropyl group, an n-butyl group, a phenyl group, a naphthyl group, a biphenyl (biphenyl) group, a 2-isopropylphenyl group, a 3,5-xylyl group, a 2,4,6-trimethylphenyl group, a benzyl group, a methoxy group, an ethoxy group, an isopropoxy group, phenoxy, a 4-tert-butylphenoxy group or a naphthoxy group; $R_2$ to $R_5$ may be linked with an adjacent substituent by

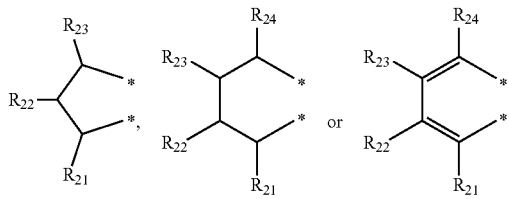

to form a fused ring, $R_{21}$ to $R_{24}$ may be each independently hydrogen, a methyl group, an ethyl group, an n-propyl group, an isopropyl group, an n-butyl group, an isobutyl group, a 2-methylbutyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl (biphenyl) group, a fluorenyl group, a triphenyl group, a naphthyl group, an anthracenyl group, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, an (n-propylphenyl)methyl group, an (isopropylphenyl)methyl group, an (n-butylphenyl)methyl group, a (sec-butylphenyl)methyl group, a (tert-butylphenyl)methyl group, an (n-pentylphenyl)methyl group, a (neopentylphenyl)methyl group, an (n-hexylphenyl)methyl group, an (n-octylphenyl)methyl group, an (n-decylphenyl)methyl group, an (n-tetradecylphenyl)methyl group, a naphthylmethyl group or an anthracenylmethyl group; $R_9$ may be an isopropyl group, an n-butyl group, an isobutyl group, a 2-methylbutyl group, a sec-butyl group, a tert-butyl group, an n-pentyl group, a cyclopropyl group, a cyclobutyl group, a cyclopentyl group, a benzyl group or a diphenylmethyl group; $R_6$ and $R_7$ may be each independently a methyl group, an ethyl group, an n-propyl group, an isopropyl group, an n-butyl group, an isobutyl group, a 2-methylbutyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl, a fluorenyl, a triphenyl, a naphthyl group, an anthracenyl group, a benzyl group, a naphthylmethyl group, an anthracenylmethyl group or a 4-methoxyphenyl group, or $R_6$ and $R_7$ may be linked by

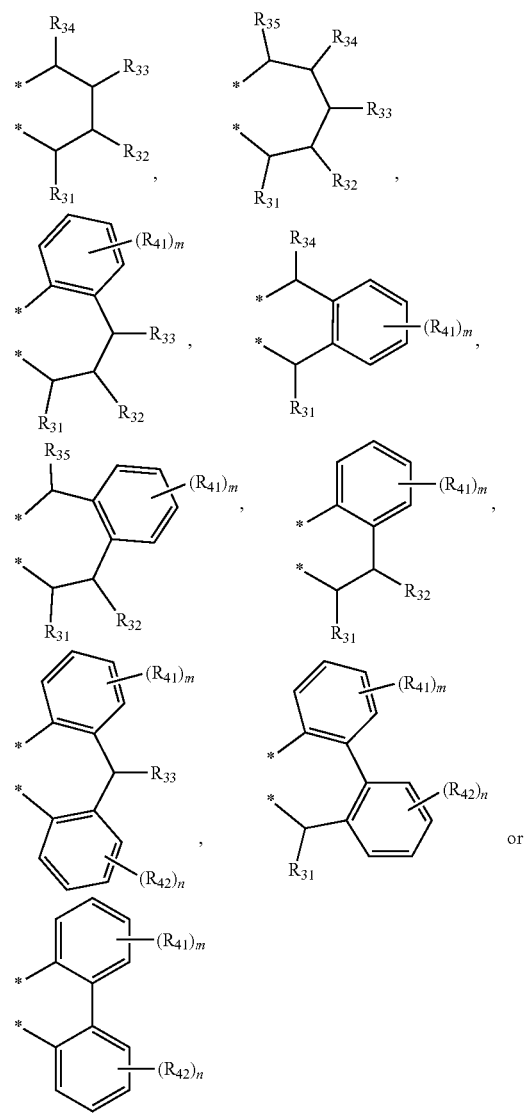

to form a ring;

$R_{31}$ to $R_{35}$, $R_{41}$ and $R_{42}$ may be each independently hydrogen, a methyl group, an ethyl group, an n-propyl group, an isopropyl group, an n-butyl group, an isobutyl group, a 2-methylbutyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl (biphenyl) group, a fluorenyl group, a triphenyl group, a naphthyl group, an anthracenyl group, a benzyl group, a naphthylmethyl group or an anthracenylmethyl group; m and n may be each independently an integer of 1 to 4; and $R_8$ may be hydrogen, a methyl group, an ethyl group, an n-propyl group, an isopropyl group, an n-butyl group, an isobutyl group, a 2-methylbutyl group or a sec-butyl group.

In an exemplary embodiment of the present invention, in the definition of the substituents $X_1$ and $X_2$, the halogen atom may be exemplified as fluorine, chlorine, bromine or iodine atom, the (C1-C20)alkyl group may be exemplified as a methyl group, an ethyl group, an n-propyl group, an isopropyl group, an n-butyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group or an n-eicosyl group; the (C3-C20)cycloalkyl group may be exemplified as a cyclopropane group, a cyclobutyl group, a cyclopentyl group, a cyclohexyl group, cycloheptyl group or an adamantyl group; the (C6-C30)aryl group may be exemplified as a phenyl group or a naphthyl group; the (C6-C30) aryl(C1-C20)alkyl group or ((C1-C20)alkyl(C6-C30)aryl) (C1-C20)alkyl group may be exemplified as a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethyl-phenyl)methyl group, a (3,4,5-trimethylphenyl)methyl group, a (2,4,6-trimethylphenyl) methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, an (n-propylphenyl) methyl group, an (isopropylphenyl)methyl group, an (n-butylphenyl)methyl group, a (sec-butylphenyl)methyl group, a (tert-butylphenyl)methyl group, an (n-pentylphenyl)methyl group, a (neopentylphenyl)methyl group, an (n-hexylphenyl)methyl group, an (n-octylphenyl)methyl group, an (n-decylphenyl)methyl group, an (n-tetradecylphenyl)methyl group, a naphthylmethyl group or an anthracenylmethyl group; the (C1-C20)alkoxy may be exemplified as a methoxy group, an ethoxy group, an n-propoxy group, an isopropoxy group, an n-butoxy group, a sec-butoxy group, a tert-butoxy group, an n-pentoxy group, a neopentoxy group, an n-hexoxy group, an n-octoxyl group, an n-dodexoxy group, an n-pentadexoxy group or an n-eicoxoxy group; the (C6-C30)aryloxy may be exemplified as a phenoxy group, a 4-tert-butylphenoxy group or a 4-methoxyphenoxy group; an example of —OSi$R^aR^bR^c$ may include a trimethylsiloxy group, a triethylsiloxy group, a tri-n-propylsiloxy group, a tri-isopropylsiloxy group, a tri-n-butylsiloxy group, a tri-sec-butylsiloxy group, a tri-tert-butylsiloxy group, a tri-isobutylsiloxy group, a tert-butyldimethylsiloxy group, a tri-n-pentylsiloxy group, a tri-n-hexylsiloxy group or a tricyclohexylsiloxy group, an example of —N$R^eR^f$ may include a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a dibenzylamino group, a methylethylamino group, a methylphenylamino group, a benzylhexylamino group, a bistrimethylsilylamino group or a bis-tert-butyldimethylsilylamino group; an example of —P$R^gR^h$ may include a dimethylphosphine group, a diethylphosphine group, a di-n-propylphosphine group, a diisopropylphosphine group, a di-n-butylphosphine group, a di-sec-butylphosphine group, a di-tert-butylphosphine group, a diisobutylphosphine group, a tert-butylisopropylphosphine group, a di-n-hexylphosphine group, a di-n-octylphosphine group, a di-n-decylphosphine group, a diphenylphosphine group, a dibenzylphosphine group, a methylethylphosphine group, a methylphenylphosphine group, a benzylhexylphosphine group, a bistrimethylsilylphosphine group or a bis-tert-butyldimethylsilylphosphine group; and an example of —S$R^d$ may include a methylthio group, an ethylthio group, a propylthio group, an isopropylthio group, a 1-butylthio group or an isopentylthio group.

In an exemplary embodiment of the present invention, $X_1$ and $X_2$ are each independently halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C1-C20)alkyl(C6-C30)aryloxy, —OSi$R^aR^bR^c$, —S$R^d$, —N$R^eR^f$ or —P$R^gR^h$; and $R^a$ to $R^h$ may be each independently (C1-C20)alkyl or (C6-C20)aryl.

In an exemplary embodiment of the present invention, more specifically, $X_1$ and $X_2$ may be each independently fluorine, chlorine, bromine, a methyl group, an ethyl group, an isopropyl group, an amyl group, a benzyl group, a methoxy group, an ethoxy group, an isopropoxy group, a tert-butoxy group, a phenoxy group, a 4-tert-butylphenoxy group, a trimethylsiloxy group, a tert-butyldimethylsiloxy group, a dimethylamino group, a diphenylamino group, a dimethylphosphine group, a diethylphosphine group, a diphenylphosphine group, an ethylthio group or isopropylthio group.

In an exemplary embodiment of the present invention, in the above Chemical Formula 2, still more preferably, M is tetravalent titanium, zirconium or hafnium; $R_1$ is (C1-C20) alkyl; $R_{11}$ to $R_{15}$ are each independently hydrogen or (C1-C20)alkyl; $R_2$ to $R_5$ may be each independently hydrogen or (C1-C20)alkyl, or $R_2$ to $R_5$ may be linked with an adjacent substituent by

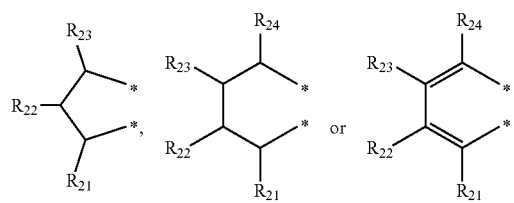

to form a fused ring; $R_{21}$ to $R_{24}$ are each independently hydrogen or (C1-C20)alkyl; $R_6$ and $R_7$ are each independently (C1-C20)alkyl, or $R_6$ and $R_7$ may be linked by

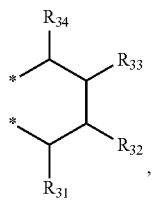 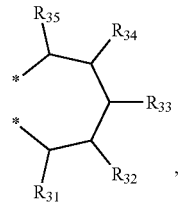

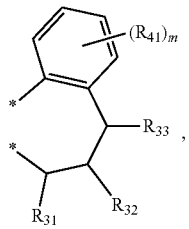 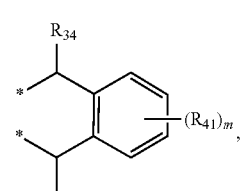

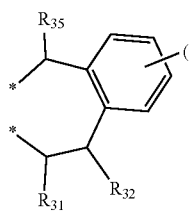 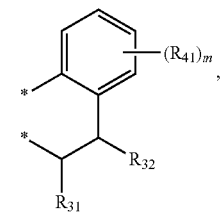

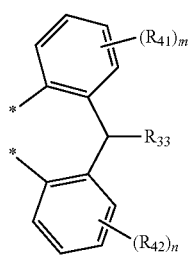 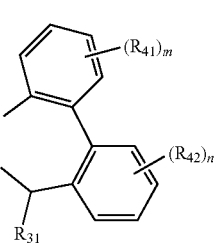 or

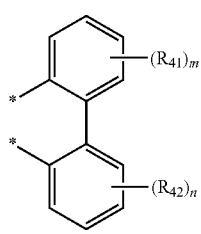

to form a ring; $R_{31}$ to $R_{35}$, $R_{41}$ and $R_{42}$ are each independently hydrogen or (C1-C20)alkyl; m and n are each independently an integer of 1 to 4; $R_9$ is (C1-C20)alkyl or (C3-C20)cycloalkyl; $X_1$ and $X_2$ are each independently halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C1-C20)alkyl(C6-C30)aryloxy, —OSiR$^a$R$^b$R$^c$, —SR$^d$, —NR$^e$R$^f$ or —PR$^g$R$^h$; and R$^a$ to R$^h$ may be each independently (C1-C20)alkyl or (C6-C20)aryl.

In an exemplary embodiment of the present invention, the transition metal complex may be selected from the compounds of the following structures, but not limited thereto:

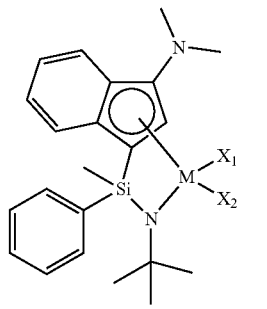

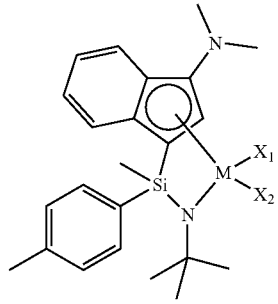

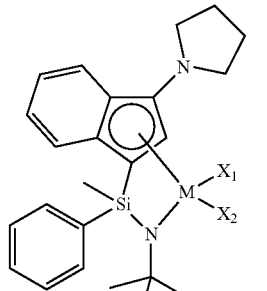

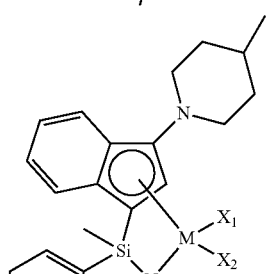

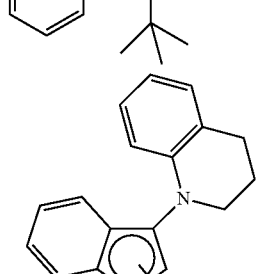

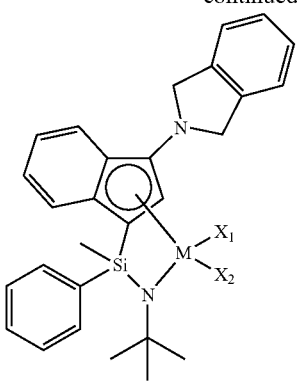
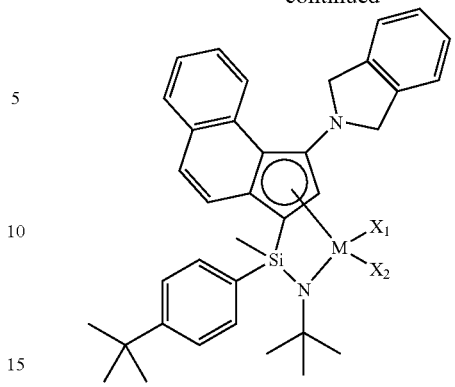
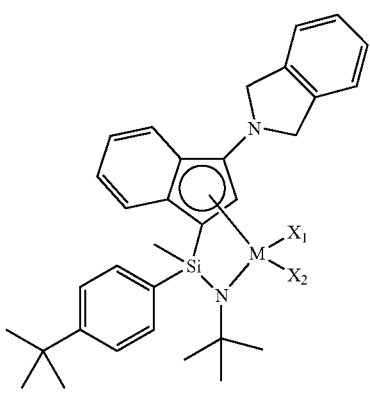
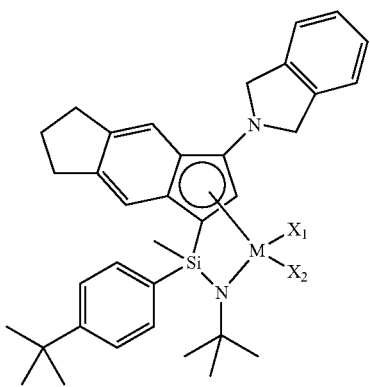
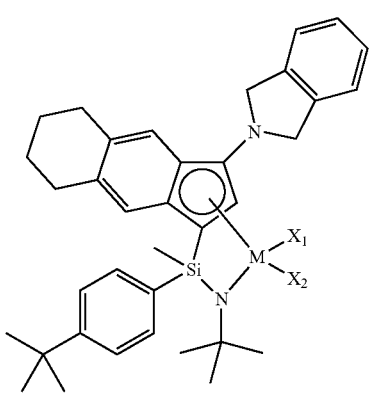

wherein M is tetravalent titanium, zirconium or hafnium;

$X_1$ and $X_2$ are each independently halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C1-C20)alkyl(C6-C30)aryloxy, —OSiR$^a$R$^b$R$^c$, —SR$^d$, —NR$^e$R$^f$ or —PR$^g$R$^h$; and R$^a$ to R$^h$ may be each independently (C1-C20)alkyl or (C6-C20)aryl.

Meanwhile, the transition metal complex according to the present invention may preferably operate together with an aluminum compound, a boron compound, or a mixture thereof which may extract an $X_1$ or $X_2$ ligand in the transition metal complex to cationize a center metal, while acting as a counter ion, i.e., an anion having weak binding force, as a cocatalyst, in order to be an active catalyst component which is used for preparation of an ethylene-based polymer selected from the group consisting of an ethylene homopolymer and copolymers of ethylene and α-olefins, and a catalyst composition including the transition metal complex and the cocatalyst is also within the scope of the present invention.

Another aspect of the present invention for achieving the above object relates to a transition metal catalyst composition including the transition metal complex, and a cocatalyst selected from the group consisting of an aluminum compound, a boron compound and a mixture thereof.

In the catalyst composition according to an exemplary embodiment of the present invention, an aluminum compound which may be used as the cocatalyst may be one or two or more selected from the group consisting of an aluminoxane compound of Chemical Formula 3 or 4, an organic aluminum compound of Chemical Formula 5, and an organic aluminum oxide compound of Chemical Formula 6 or 7:

| | |
|---|---|
| (—Al(R$_{51}$)—O—)$_p$ | Chemical Formula 3 |
| (R$_{51}$)$_2$Al—O—Al(R$_{51}$)$_2$ | Chemical Formula 4 |
| (R$_{52}$)$_{3-r}$Al(E)$_r$ | Chemical Formula 5 |
| (R$_{53}$)$_2$AlOR$_{54}$ | Chemical Formula 6 |
| R$_{53}$Al(OR$_{54}$)$_2$ | Chemical Formula 7 | wherein R$_{51}$ is (C1-C20)alkyl, preferably a methyl group or an isobutyl group, p is an integer of 5 to 20; R$_{52}$ and R$_{53}$ are (C1-C20)alkyl, respectively; E is hydrogen or halogen; r is an integer of 0 to 3; R$_{54}$ is (C1-C20)alkyl or (C6-C30)aryl.

A specific example which may be used as the aluminum compound may include methylaluminoxane, modified methylaluminoxane, and tetraisobutylaluminoxane as an aluminoxane compound; trialkylaluminum including trimethylaluminum, triethylaluminum, tripropylaluminum, triisobutylaluminum and trihexylaluminum; dialkylaluminumchloride including dimethylaluminumchloride, diethylaluminumchloride, dipropylaluminum chloride, diisobutylaluminumchloride and dihexylaluminumchloride; alkyl aluminumdichloride including methylaluminumdichloride, ethylaluminumdichloride, propylaluminumdichloride, isobutylaluminumdichloride and hexylaluminumdichloride; dialkylaluminum hydride including dimethylaluminum hydride, diethylaluminum hydride, dipropylaluminum hydride, diisobutylaluminum hydride and dihexylaluminum hydride, as an organic aluminum compound.

In an exemplary embodiment of the present invention, the aluminum compound may be one or a mixture of two or more selected from the group consisting of an alkylaluminoxane compound and trialkylaluminum, and more preferably one or a mixture of two or more selected from the group consisting of methylaluminoxane, modified methylaluminoxane, tetraisobutylaluminoxane, trimethylaluminum, triethylaluminum, trioctylaluminum and triisobutylaluminum.

In the catalyst composition according to an exemplary embodiment of the present invention, the boron compound which may be used as the cocatalyst is known in U.S. Pat. No. 5,198,401, and may be selected from the compounds represented by the following Chemical Formulae 8 to 10:

B(R61)3    Chemical Formula 8

[R62]+[B(R61)4]—    Chemical Formula 9

[(R63)2Ar2ZH]+[B(R61)4]—    Chemical Formula 10 wherein B is a boron atom; R61 is a phenyl group, in which the phenyl group may be further substituted by 3 to 5 substituents selected from the group consisting of fluoro, (C1-C20)alkyl unsubstituted or substituted by fluoro, (C1-C20)alkoxy unsubstituted or substituted by fluoro; R62 is a (C5-C7)aromatic radical or a (C1-C20)alkyl(C6-C20)aryl radical, a (C6-C30)aryl(C1-C20)alkyl radical, for example, triphenylmethylinium(triphenylmethylium) radical; Z is a nitrogen or phosphorus atom; R63 is a (C1-C20)alkyl radical, and Ar2 is phenyl or a (C5-C7)aromatic radical substituted by a (C1-C20)alkyl group.

A preferred example of the boron-based cocatalyst may include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5,6-tetrafluorophenyl)borate, tetrakis(2,2,4-trifluorophenyl)borate, phenylbis(pentafluorophenyl)borate or tetrakis(3,5-bistrifluoromethylphenyl)borate. In addition, a specific combination example thereof may include ferrocenium tetrakis(pentafluorophenyl)borate, 1,1'-dimethylferrocenium tetrakis(pentafluorophenyl)borate, tetrakis(pentafluorophenyl)borate, triphenylmethylinium tetrakis(pentafluorophenyl)borate, triphenylmethylinium tetrakis(3,5-bistrifluoromethylphenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-ditetradecylanilinium tetrakis(pentafluorophenyl)borate, N,N-dihexadecylanilinium tetrakis(pentafluorophenyl)borate, N,N-dioctadecylanilinium tetrakis(pentafluorophenyl)borate, N,N-2,4,6-pentamethylanilinium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, or tri(dimethylphenyl)phosphonium tetrakis(pentafluorophenyl)borate, and among them, the most preferred one is N,N-dimethyl anilinium tetrakis(pentafluorophenyl)borate, triphenylmethylinium tetrakis(pentafluorophenyl)borate, N,N-ditetradecylanilinium tetrakis(pentafluorophenyl)borate, N,N-dihexadecylanilinium tetrakis(pentafluorophenyl)borate, N,N-dioctadecylanilinium tetrakis(pentafluorophenyl)borate, or tris(pentafluoro)borane.

Meanwhile, the cocatalyst may serve as a scavenger which removes impurities acting as a poison to the catalyst in the reactant.

In an exemplary embodiment according to the present invention, when the aluminum compound is used as the cocatalyst, a preferred range of the ratio between the transition metal complex of the present invention and the cocatalyst may be 1:1-2,000, based on a mole ratio of the transition metal (M):the aluminum atom (Al).

In an exemplary embodiment according to the present invention, when both the aluminum compound and the boron compound are used as the cocatalyst, a preferred range of the ratio between the transition metal complex of the present invention and the cocatalyst may be 1:0.1-100:1-2,000, preferably in a range of 1:0.5-30:10-1,000, more preferably in a range of 1:0.5-5:10-500, based on a mole ratio of the center metal (M):boron atom (B):aluminum atom (Al).

When the ratio between the transition metal complex of the present invention and the cocatalyst is out of the above range, the amount of the cocatalyst is relatively small so that activation of the transition metal complex is not completely achieved, and thus, the catalyst activity of the transition metal complex may not be sufficient, or the cocatalyst is used more than necessary to greatly increase production costs. Within the above range, excellent catalyst activity for preparing an ethylene homopolymer or copolymers of ethylene and α-olefins is represented, and the range of the ratio is varied with the purity of the reaction.

Another aspect of the present invention for achieving the above object relates to a method for preparing an ethylene-based polymer selected from the group consisting of an ethylene homopolymer and copolymers of ethylene and α-olefins, using the transition metal complex or the transition metal catalyst composition.

Another aspect of the present invention for achieving the above object relates to a copolymerization method for copolymerizing ethylene, propylene and optionally a non-conjugated diene, using the transition metal complex or the transition metal catalyst composition.

The method for preparing the ethylene-based polymer using the transition metal catalyst composition may proceed by bring the transition metal catalyst, the cocatalyst, and ethylene or an α-olefin comonomer into contact in the presence of a suitable organic solvent. Here, the transition metal catalyst and the cocatalyst components may be added to a reactor separately, or each component may be mixed previously and added to a reactor, and mixing conditions such as an addition order, temperature or concentration is not particularly limited.

A preferred organic solvent which may be used in the preparation method may be (C3-C20) hydrocarbons, and a specific example thereof may include butane, isobutane, pentane, hexane, heptane, octane, isooctane, nonane, decane, dodecane, cyclohexane, methylcyclohexane, benzene, toluene, xylene, or the like.

Specifically, when the ethylene homopolymer is prepared alone, ethylene is used as a monomer alone, in which appropriate ethylene pressure may be 1-1,000 atm, more preferably 6-150 atm. In addition, a polymerization reaction temperature of 25° C.-220° C., preferably 70° C.-220° C., and more preferably 100° C.-220° C. is effective.

In addition, when copolymers of ethylene and α-olefins are prepared, C3-C18 α-olefins, C4-C20 diolefins, C5-C20 cycloolefins or cyclodiolefins, or styrene and a derivative thereof may be used as a comonomer together with ethylene, and a preferred example of C3-C18 α-olefins may be selected from the group consisting of propylene, 1-butene, 1-pentene, 4-methyl-1-pentene, 1-hexene, 1-octene, 1-decene, 1-dodecene, 1-hexadecene and 1-octadecene, a preferred example of C4-C20 diolefins may be selected from the group consisting of 1,3-butadiene, 1,4-pentadiene and 2-methyl-1,3-butadiene, and a preferred example of C5-C20 cycloolefins or cyclodiolefins may be selected from the group consisting of cyclopentene, cyclohexene, cyclopentadiene, cyclohexadiene, norbornene, 5-vinylidene-2-norbornene(VNB), 5-methylene-2-norbornene(MNB) and 5-ethylidene-2-norbornene(ENB). In the present invention, the olefin may be homopolymerized or two or more olefins may be copolymerized. In this case, preferred ethylene pressure and polymerization temperature may be identical to those in the preparation of the ethylene homopolymer, and the copolymer prepared according to the method of the present invention contains usually 30 wt % or more of ethylene, preferably 60 wt % or more of ethylene, and more preferably 60 to 99 wt % of ethylene.

As described above, when the catalyst of the present invention is used, polymers in a scope from an elastomer to a high density polyethylene (HDPE), having a density of 0.850 g/cc to 0.960 g/cc and a melt flow rate of 0.001 to 2000 dg/min may be easily and economically prepared, by appropriately using ethylene and C3-C10 α-olefins as a comonomer.

In addition, an ethylene/propylene (EP) elastomer and an ethylene/propylene/diene (EPDM) elastomer may be well prepared, using the catalyst of the present invention. In particular, since a high-priced diene is easily injected, an EPDM product having a Mooney viscosity (ASTM D1646-94, ML1+4@125° C.) adjusted to 1 to 250, preferably 10 to 200 may be easily prepared in an economical manner.

Further, for adjusting a molecular weight when preparing the ethylene homopolymer or copolymer according to the present invention, hydrogen may be used as a molecular weight regulator, and the polymer usually has a weight average molecular weight (Mw) in a range of 5,000 to 1,000,000 g/mol.

Since the catalyst composition presented in the present invention is present in a homogeneous form in a polymerization reactor, it is preferred to apply the catalyst composition to a solution polymerization process which is carried out at a temperature equal to or more than a melting point of the polymer. However, as disclosed in U.S. Pat. No. 4,752,597, the catalyst composition may be used in a slurry polymerization or gas phase polymerization process as a heterogeneous catalyst system by supporting the transition metal complex and the cocatalyst on a porous metal oxide support.

In addition, the present invention also includes the compound represented by the following Chemical Formula Int-1 as an intermediate for preparing the transition metal complex of Chemical Formula 1:

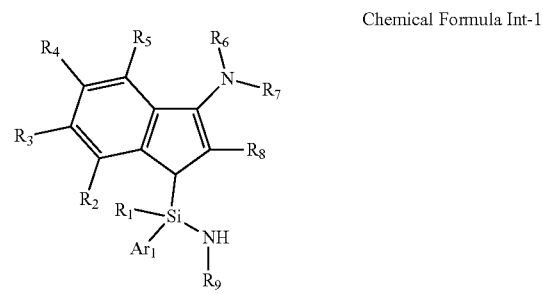

Chemical Formula Int-1 wherein $R_1$ to $R_9$ and $Ar_1$ are as defined in the above Chemical Formula 1.

In addition, the present invention relates to the transition metal complex of Chemical Formula 1 for use in preparing copolymers of ethylene and α-olefins having a unimodal GPC graph, and a method for preparing copolymers of ethylene and α-olefins which, as a result of TGIC analysis using the transition metal complex, represent a chemical composition distribution as a unimodal or bimodal graph.

Hereinafter, the present invention will be described in detail by the following Examples, however, the scope of the present invention is not limited thereto.

Unless otherwise stated, all experiments of synthesizing ligands and catalysts were carried out using a standard Schlenk or glove box technology under a nitrogen atmosphere, and an organic solvent used in the reaction was refluxed under a sodium metal and benzophenone to remove moisture, and used after being distilled immediately before use. The $^1$H NMR analysis of the synthesized ligand and the catalyst was carried out using Bruker 500 MHz at room temperature.

Cyclohexane as a polymerization solvent was used after sufficiently removing moisture, oxygen and other catalyst poisoning materials therefrom by passing cyclohexane through a 5 Å molecular sieve and a tube filled with active alumina, and bubbling cyclohexane with high purity nitrogen. The polymerized polymer was analyzed by the methods described below:

1. Melt Flow Index (MI)

Measured according to ASTM D 2839.

2. Density

Measured according to ASTM D 1505, using a density gradient tube.

3. C2 Conversion (%) Analysis

Content ratios of unreacted ethylene and nitrogen as a standard material were measured using gas chromatography (GC).

4. Molecular Weight and Molecular Weight Distribution

Measured at 135° C. at a rate of 1.0 mL/min, in an 1,2,3-trichlorobenzene solvent, using PL210 GPC equipped with PL Mixed-BX2+preCol, the molecular weight being corrected using a PL polystyrene standard material.

Preparation Example 1

Preparation of Complex 1

Preparation of Compound 1-a

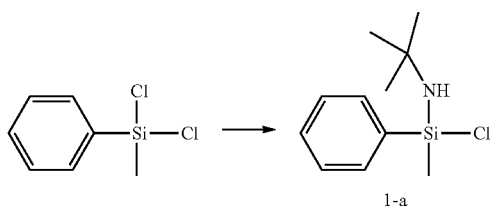

1-a

Under the nitrogen atmosphere, dichloro(methyl)(phenyl)silane (30 g, 157.0 mmol) was dissolved in normal hexane (400 mL) in a 500 mL round flask. tert-Butylamine (23.0 g, 314.0 mmol) was slowly added thereto with vigorous stirring, and stirred for 12 hours. The solid content was removed by a filter filled with dried celite. The solvent was removed in vacuo to obtain Compound 1-a as colorless liquid (5.0 g, an yield of 94.2%).

$^1$H-NMR (500 MHz, $C_6D_6$, ppm): δ 0.483 (s, 3H), 1.040 (s, 10H), 7.038-7.291 (m, 3H), 7.713-7.879 (m, 2H)

Preparation of Compound 1-b

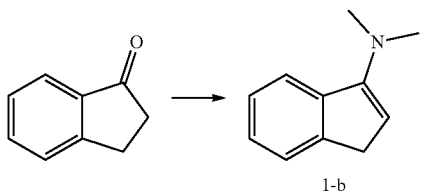

1-b

Under the nitrogen atmosphere, 2,3-dihydro-1H-inden-1-one (5 g, 37.8 mmol) was dissolved in anhydrous normal hexane (150 mL) in a 250 mL round flask, and then tetrakis(dimethylamino)titanium (4.7 g, 20.8 mmol) was added thereto with stirring and stirred for 12 hours, thereby producing a yellow solid content. The solid content was removed by a filter filled with dried celite. The solvent was removed in vacuo to obtain liquid Compound 1-b (5.0 g, an yield of 83.0%).

Preparation of Compound 1-c

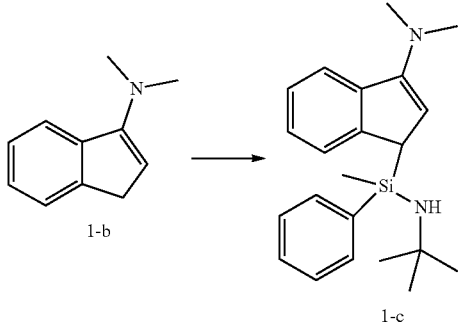

1-c

Under the nitrogen atmosphere, Compound 1-b (5.0 g, 31.4 mmol) was dissolved in 150 mL of anhydrous normal hexane in a 250 mL round flask, 1.6 M normal butyl lithium (19.6 mL, 31.4 mmol) was added thereto, stirred for 12 hours, and then the solution was removed by filtering. The solid content was dissolved in tetrahydrofuran (THF) (100 mL), and then added to a 250 mL round flask and stirred. N-tert-butyl-1-chloro-1-methyl-1-phenylsilaneamine (7.16 g, 31.4 mmol) was dissolved in tetrahydrofuran (THF) (50 mL) and added, and then stirred at room temperature for 12 hours. The solvent was removed in vacuo, and dissolved by adding normal hexane (150 mL), and then the solid content was removed by a filter filled with dry celite. The solvent was all removed to obtain Compound 1-c as viscous oil (10.0 g, an yield of 90.8%, a ratio of diastereomers of 1:1).

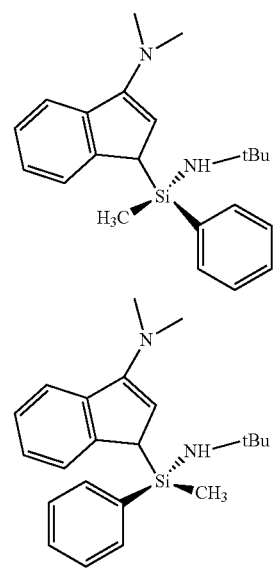

$^1$H-NMR (500 MHz, $C_6D_6$, ppm): δ 0.076 (d, 3H), 0.953 (d, 9H), 2.532 (m, 6H), 3.076 (s, 1H), 3.475-3.531 (m, 1H), 5.499 (d, 1H), 7.098-7.569 (m, 9H)

Preparation of Compound 1-d

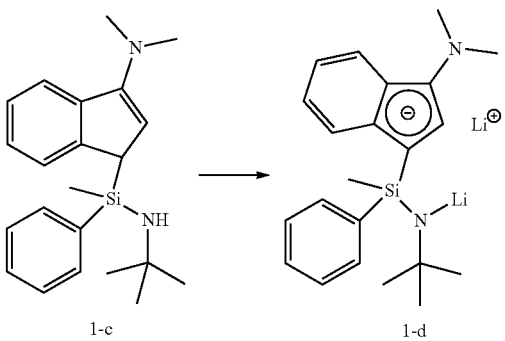

1-c      1-d

Under the nitrogen atmosphere, Compound 1-c (5.1 g, 14.6 mmol) was dissolved in normal hexane (150 mL) in a 250 mL round flask. 1.6 M normal butyl lithium (19.1 mL, 30.6 mmol) was added thereto at room temperature, stirred for 12 hours, filtered to separate the solid content, and then dried in vacuo, thereby obtaining Compound 1-d (5 g, yield: 94.8%), which was used directly in the next reaction.

Preparation of Complex 1

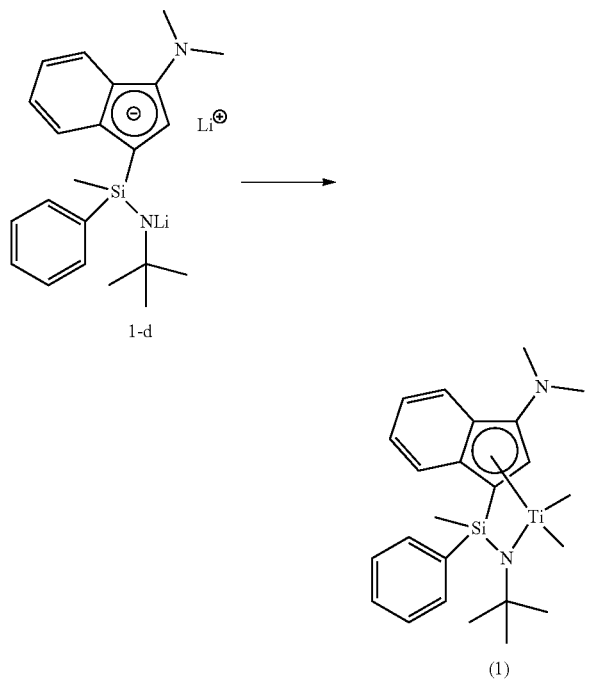

Under the nitrogen atmosphere, Compound 1-d (4.0 g, 11.0 mmol) was dissolved in diethyl ether (50 mL) in a 250 mL three neck round flask, the temperature was lowered to −78° C., 1.5 M methyl lithium (14.7 mL, 22.1 mmol) was slowly injected thereinto, and a solution of tetrachlorotitanium (TiCl$_4$) (2.1 g, 11.0 mmol) diluted with anhydrous normal hexane (30 mL) was slowly added thereto at −78° C. The reactant was stirred at room temperature for 3 hours, and then the solvent was removed in vacuo. The reactant was dissolved in normal hexane (100 mL) again, and the solid content was removed by a filter filled with dried celite. The solvent was all removed to obtain Complex 1 in a red (4.2 g, yield: 89.2%, a ratio of diastereomers of 1:1).

$^1$H-NMR (500 MHz, C$_6$D$_6$, ppm): δ 0.055 (d, 3H), 0.730-1.391 (m, 6H), 1.474 (d, 9H), 2.573 (d, 6H) 5.499 (d, 1H), 6.631-7.837 (m, 9H)

Preparation Example 2

Preparation of Complex 2

Preparation of Compound 2-a

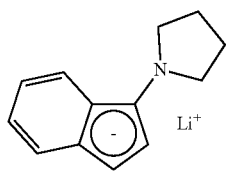

Compound 2-a was prepared by the preparation method of U.S. Pat. No. 6,268,444 B 1.

Preparation of Compound 2-b

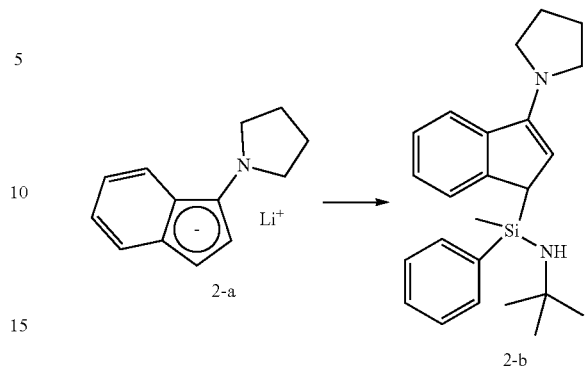

Under the nitrogen atmosphere, Compound 2-a (6.00 g, 31.4 mmol) was added to a 250 mL round flask, and 150 mL of THF was added thereto, and stirred. N-tert-butyl-1-chloro-1-methyl-1-phenylsilaneamine (7.16 g, 31.4 mmol) was dissolved in tetrahydrofuran (THF) (50 mL), and added, and then stirred at room temperature for 12 hours. The solvent was removed in vacuo, and dissolved by adding normal hexane (150 mL), and then the solid content was removed by a filter filled with dry celite. The solvent was all removed to obtain Compound 2-b as viscous oil (10.8 g, an yield of 91.0%, a ratio of diastereomers of 1:1).

$^1$H-NMR (500 MHz, C$_6$D$_6$, ppm): δ 0.156 (d, 3H), 0.703-0.830 (m, 1H), 0.976 (d, 9H), 1.501-1.528 (m, 4H), 3.089-3.217 (m, 4H), 3.501-3.604 (m, 1H), 5.259 (d, 1H), 7.034-7.652 (m, 9H)

Preparation of Complex 2

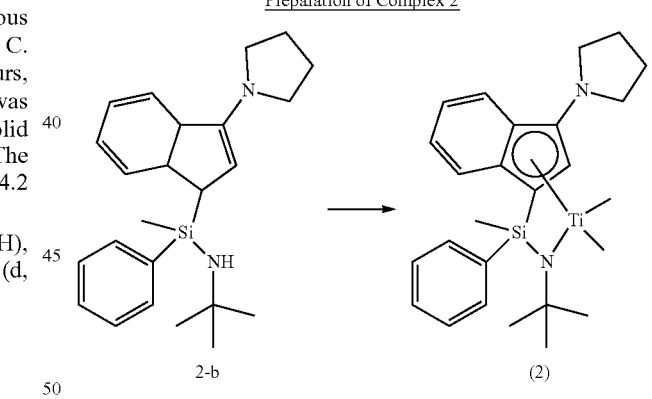

Under the nitrogen atmosphere, Compound 2-d (4.14 g, 11.0 mmol) was dissolved in diethyl ether (50 mL) in a 250 mL three neck round flask, the temperature was lowered to −78° C., and 1.5 M methyl lithium (29.4 mL, 44.2 mmol) was slowly injected thereinto. The temperature was raised to room temperature, and the reactant was stirred for 6 hours. The reactant was cooled to a temperature of −78° C. again, and a solution of tetrachlorotitanium (TiCl$_4$) (2.1 g, 11.0 mmol) diluted with anhydrous normal hexane (30 mL) was slowly added thereto at −78° C. The reactant was stirred at room temperature for 3 hours, and then the solvent was removed in vacuo. The reactant was dissolved in normal hexane (100 mL) again, and the solid content was removed by a filter filled with dried celite. The solvent was all removed to obtain Complex 2 in a red (4.14 g, yield: 83.2%, a ratio of diastereomers of ~1:3).

¹H-NMR (500 MHz, C₆D₆, ppm): δ 0.153 (d, 3H), 0.702-0.950 (m, 6H), 1.490 (d, 9H), 2.951-3.442 (m, 8H), 5.360 (d, 1H), 6.698-7.890 (m, 9H)

Preparation Example 3

Preparation of Complex 3

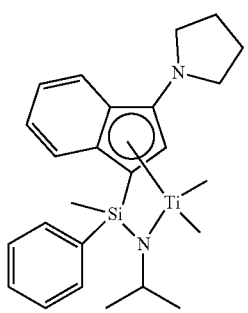

(3)

Reaction was carried out in the same manner as the preparation method of Complex 2 of Preparation Example 2, except for using N-isopropyl-1-chloro-1-methyl-1-phenylsilaneamine (31.4 mmol) instead of N-tert-butyl-1-chloro-1-methyl-1-phenylsilaneamine (7.16 g, 31.4 mmol), thereby preparing Complex 3 (3.54 g, yield: 75.3%, a ratio of diastereomers of 1:2).

¹H-NMR (500 MHz, C₆D₆, ppm): δ 0.071 (d, 3H), 0.660-0.851 (m, 6H), 1.196-1.604 (m, 10H), 2.843-3.422 (m, 4H), 4.133-4.668 (m, 1H), 5.380 (d, 1H), 6.635-7.813 (m, 9H)

Comparative Preparation Example 1

Preparation of (t-butylamido)dimethyl(tetramethyl-cyclopentadienyl)silanetitanium (IV) dimethyl

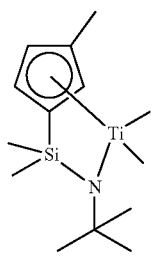

A (t-butylamido)dimethyl(tetramethylcyclopentadienyl)silanetitanium(IV) dimethyl compound was prepared by dissolving (t-butylamido)dimethyl(tetramethylcyclopentadienyl)silanetitanium(IV) dichloride purchased from Boulder Scientific, U.S.A. in diethyl ether, which was cooled to a temperature of −78° C., and reacted with 2 equivalents of methyl lithium.

Comparative Preparation Example 2

Preparation of Complex A

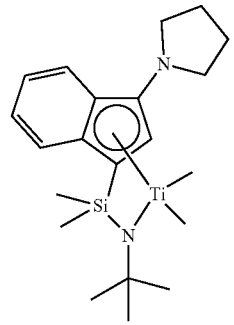

(A)

Complex A was prepared by the preparation method of U.S. Pat. No. 6,268,444 B 1.

Comparative Preparation Example 3

Preparation of Complex B

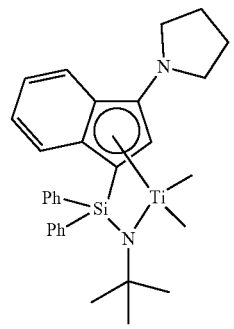

(B)

Complex B was prepared by the preparation method of WO 01/42315 A1.

Comparative Preparation Example 4

Preparation of Complex C

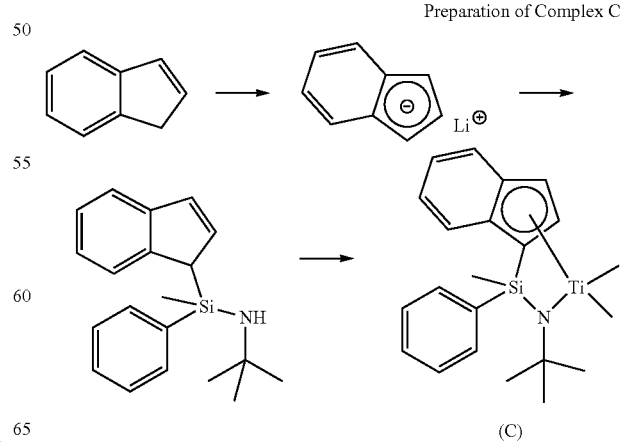

(C)

Complex C was prepared from 1H-indene by the preparation method of Complex 2 of Preparation Example 2.

$^1$H-NMR (500 MHz, $C_6D_6$, ppm): 6-0.131 (d, 3H), 0.404 (d, 3H), 0.825 (d, 3H), 1.455 (d, 9H) 6.101-6.126 (m, 1H), 7.010-7.531 (m, 10H)

Copolymerization of ethylene and 1-octene

Examples 1-7 and Comparative Examples 1-2

Copolymerization of Ethylene and 1-Octene by Continuous Solution Process

Copolymerization of ethylene and 1-octene was carried out using continuous polymerization equipment, as follows.

The catalysts synthesized in Preparation Examples 1-3 and Comparative Preparation Example 1 were used as a single active site catalyst, cyclohexane was used as a solvent, and the used amount of the catalyst was as described in the following Table 1. Ti represents the catalyst, Al represents triisobutylaluminum, and B represents N,N-dioctadecylanilinium tetrakis(pentafluorophenyl)borate which is the cocatalyst, respectively. Synthesis was carried out by dissolving the catalyst in toluene at a concentration of 0.1 g/L and injecting it, and using 1-octene as the comonomer. The conversion rate of the reactor was able to be assumed by the reaction condition and the temperature gradient in the reactor when polymerization was carried out with one polymer under each reaction condition. The molecular weight was controlled by the function of the reactor temperature and the 1-octene content, and the conditions and the results are shown in the following Tables 1 and 2:

TABLE 1

Results of continuous polymerization reaction using complexes prepared in Preparation Examples 1 and 2 as polymerization catalyst

| | | Example 1 | Example 2 | Example 3 | Example 4 |
|---|---|---|---|---|---|
| Polymerization conditions | Catalyst | Preparation Example 1 | Preparation Example 1 | Preparation Example 2 | Preparation Example 2 |
| | Total solution flow rate (kg/h) | 5 | 5 | 5 | 5 |
| | Ethylene input (wt %) | 10 | 12 | 8 | 10 |
| | Input mole ratio of 1-octene and ethylene (1-C8/C2) | 0.5 | 0.4 | 0.5 | 0.3 |
| | Ti input (µmol/kg) | 7.5 | 6.0 | 6.0 | 4.8 |
| | Ar/Ti ratio | 27 | 33 | 40 | 40 |
| | B/Ti ratio | 3 | 3 | 3 | 4 |
| | Reaction temperature (° C.) | 160 | 150 | 150 | 181 |
| Polymerization results | C2 conversion rate (%) | 97 | 77 | 80 | 75 |
| | MI | 4.7 | 0.07 | 1.08 | 0.66 |
| | Density (g/cc) | 0.853 | 0.882 | 0.868 | 0.893 |

TABLE 2

Results of continuous polymerization reaction using complexes prepared in Preparation Examples 2 and 3 and Comparative Preparation Example 1 as polymerization catalyst

| | | Example 5 | Example 6 | Example 7 | Comparative Example 1 | Comparative Example 2 |
|---|---|---|---|---|---|---|
| Polymerization conditions | Catalyst | Preparation Example 2 | Preparation Example 3 | Preparation Example 2 | Comparative Preparation Example 1 | Comparative Preparation Example 1 |
| | Total solution flow rate (kg/h) | 3.2 | 3.2 | 5 | 5 | 5 |
| | Ethylene input (wt %) | 8 | 8 | 10 | 8 | 10 |
| | Input mole ratio of 1-octene and ethylene (1-C8/C2) | 0.5 | 0.5 | 0.4 | 0.19 | 0.2 |
| | Ti input (µmol/kg) | 9.8 | 10 | 4.1 | 1.5 | 6.0 |
| | Ar/Ti ratio | 30 | 30 | 73 | 200 | 30 |
| | B/Ti ratio | 4 | 3 | 5 | 3 | 8 |
| | Reaction temperature (° C.) | 150 | 150 | 150 | 104 | 150 |
| Polymerization results | C2 conversion rate (%) | 99 | 99 | 99 | 92 | 96 |
| | MI | 6.88 | 2.58 | 0.08 | 5.0 | Unmeasurable (high MI) |
| | Density (g/cc) | 0.865 | 0.865 | 0.879 | 0.878 | — |
| | Mw (×10$^{-3}$) | 99 | 119 | — | — | — |
| | MWD | 2.33 | 2.20 | — | — | — |

Ti: refers to Ti in the catalyst
Al: represents a cocatalyst, triisobutylaluminum.
B: represents a cocatalyst, N,N-dioctadecylanilinium tetrakis(pentafluorophenyl)borate.

As seen from the above Tables 1 and 2, Examples 1 to 7 in which polymerization was carried out with the catalysts developed in the present invention were able to easily produce polymers having a high conversion rate of ethylene, low density and a low MI value meaning a high molecular weight even under the condition of high temperature (150° C. or more), as compared with Comparative Examples 1 and 2.

In particular, Example 7 showed a high ethylene conversion rate despite using a small amount of the catalyst as compared with Comparative Example 2, and thus, it was found that the catalyst of the present invention has excellent catalyst activity. In addition, Example 4 easily produced a copolymer having low density and a high molecular weight even at a polymerization temperature of 181° C.

That is, when the complex of the present invention is used as the polymerization catalyst, a copolymer having a high ethylene conversion rate of 77% or more, low density of 0.893 g/cc or less and a MI value less than 5 may be prepared, when carrying out polymerization at a high temperature of 150° C. or more.

Figure 2:
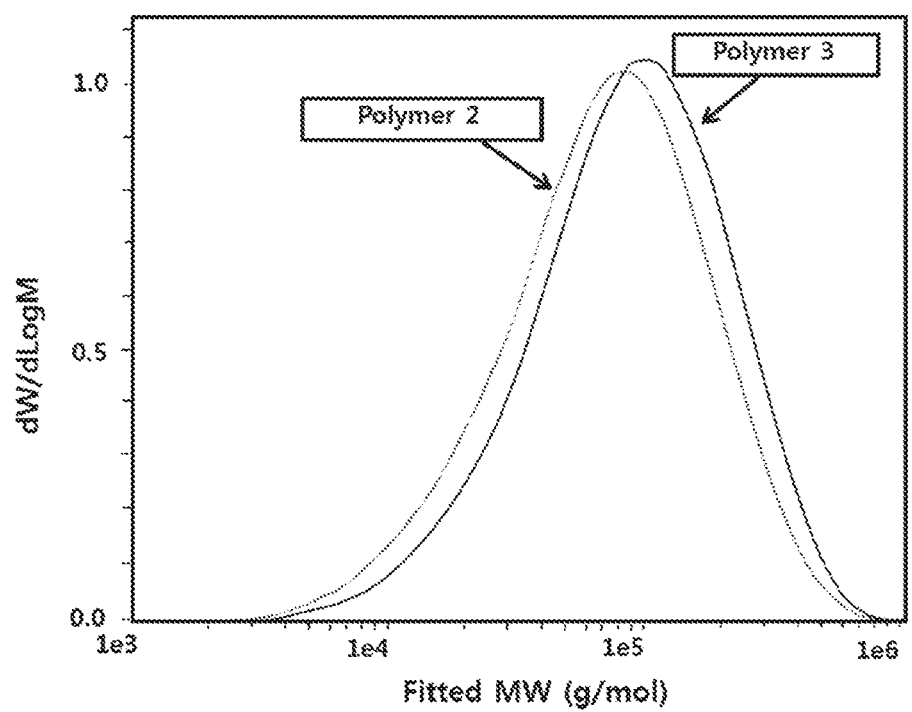
FIG. 2 is a GPC graph of the copolymers prepared in Examples 5 and 6 [Polymer 2: a polymer obtained using the complex of Preparation Example 2 as a polymerization catalyst, that is, a polymer prepared in Example 5/Polymer 3: a polymer obtained using the complex of Preparation Example 3 as a polymerization catalyst, that is, a polymer prepared in Example 6].

Meanwhile, a GPC graph of the copolymer prepared in Examples 5 and 6 is shown in FIG. 2, and a number average molecular weight (Mn), a weight average molecular weight (Mw), and a molecular weight distribution index (MWD) are described in the following Table 3:

TABLE 3

|  | Catalyst | Mn (×10$^{-3}$) | Mw (×10$^{-3}$) | MWD |
| --- | --- | --- | --- | --- |
| Example 5 | Preparation Example 2 | 42 | 99 | 2.33 |
| Example 6 | Preparation Example 3 | 54 | 119 | 2.20 |

In general, a GPC graph of copolymers prepared with the diastereomers as the catalyst has a characteristic of being broad or having a 2 peak graph shape and a broad molecular weight distribution, and the copolymers prepared in Examples 5 and 6 using the complexes of Preparation Examples 2 and 3 of the present invention as the polymerization catalyst uniquely represented a unimodal, narrow molecular weight distribution on a GPC graph. The copolymer (Polymer 2) of Example 5 represented a molecular weight distribution of 2.33, and the copolymer of Example 6 (Polymer 3) represented a molecular weight distribution of 2.2, and both of them showed a unimodal, narrow molecular weight distribution.

Figure 3:
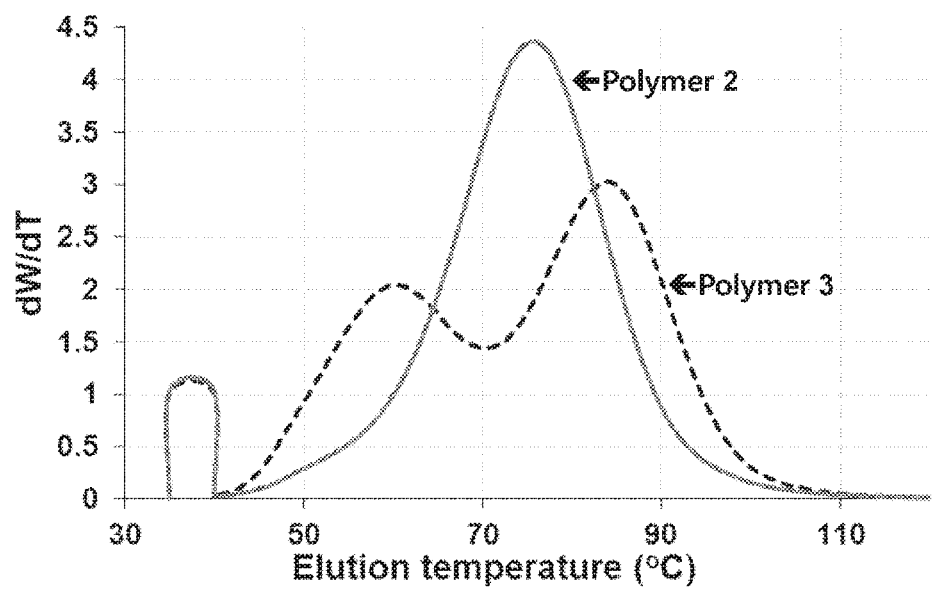
FIG. 3 is a TGIC graph of the copolymers prepared in Examples 5 and 6 [Polymer 2: a polymer obtained using the complex of Preparation Example 2 as a polymerization catalyst, that is, a polymer prepared in Example 5/Polymer 3: a polymer obtained using the complex of Preparation Example 3 as a polymerization catalyst, that is, a polymer prepared in Example 6].

In addition, FIG. 3 illustrates a thermal gradient interaction chromatography (TGIC) graph for finding out a chemical composition distribution (CCD) of copolymers prepared in Examples 5 and 6. It was found from FIG. 3 that in Example 5, the copolymer (Polymer 2) prepared using Complex 2 of Preparation Example 2 as the polymerization catalyst represents a narrow chemical composition distribution of a single peak which is a characteristic of a typical single active site catalyst, and in Example 6, the copolymer (Polymer 3) prepared using the Complex 3 of Preparation Example 3 as the polymerization catalyst represents a double peak, broad chemical composition distribution which is difficult to be obtained from a typical single active site catalyst.

Examples 8-10 and Comparative Examples 3-6

Copolymerization of Ethylene and 1-Octene Using Batchwise Polymerization Equipment Copolymerization of ethylene and 1-octene was carried out using batchwise polymerization equipment, as follows.

To a stainless steel reactor having a 1500 mL volume substituted by nitrogen after sufficient drying, 600 mL of methyl cyclohexane and 50-100 mL of 1-octene were added, 1 mL of 1.0 M hexane solution of triisobutyl aluminum was added to the reactor. Thereafter, the reactor was heated, and 0.1 mL of a titanium (IV) compound (1.0 wt % of toluene solution) synthesized in Preparation Examples 1 and 2, and Comparative Examples 2 to 4, and 0.6 mL of 10 mM toluene solution of triphenylmethylinium tetrakis(pentafluorophenyl)borate (99%, Boulder Scientific) were sequentially added. Then the pressure in the reactor was filled with ethylene to 20 kg/cm$^2$, and ethylene was continuously supplied for polymerization. The reaction proceeded for 5 minutes, and then the collected reaction product was dried for 8 hours in a vacuum oven at 40° C. The reaction temperature, ΔT, catalyst activity, density and a molecular weight are described in the following Table 4.

TABLE 4

Results of polymerization using complexes prepared in Preparation Examples 1 and 2 and Comparative Preparation Example 2-4 as polymerization catalyst, and batchwise polymerization equipment

|  | Catalyst | Used catalyst amount (μmol) | Reaction temperature (° C.) | ΔT (° C.) | Catalyst activity (polymer(kg)/ used catalyst amount (mmol)) | Density (g/cc) | Mw (×10$^{-3}$) | PDI |
| --- | --- | --- | --- | --- | --- | --- | --- | --- |
| Example 8 | Preparation Example 1 | 2 | 79.0 | 48.5 | 14.3 | — | — | — |
| Example 9 | Preparation Example 2 | 2 | 75.5 | 47.3 | 14.9 | — | — | — |
| Example 10 | Preparation Example 2 | 2 | 99.0 | 38.4 | 18.6 | 0.901 | — | — |
| Comparative Example 3 | Comparative Preparation Example 2 | 2 | 98.9 | 20.5 | 10.0 | 0.905 | 550 | 3.83 |
| Comparative Example 4 | Comparative Preparation Example 3 | 2 | 99.1 | 20.0 | 9.3 | 0.903 | 715 | 2.56 |
| Comparative Example 5 | Comparative Preparation Example 3 | 3 | 99.2 | 32.7 | 9.3 | — | — | — |

TABLE 4-continued

Results of polymerization using complexes prepared in Preparation Examples 1 and 2 and Comparative Preparation Example 2-4 as polymerization catalyst, and batchwise polymerization equipment

|  | Catalyst | Used catalyst amount (μmol) | Reaction temperature (° C.) | ΔT (° C.) | Catalyst activity (polymer(kg)/ used catalyst amount (mmol)) | Density (g/cc) | Mw (×10$^{-3}$) | PDI |
|---|---|---|---|---|---|---|---|---|
| Comparative Example 6 | Comparative Preparation Example 4 | 2 | 99.2 | 30.6 | 13.6 | 0.900 | 274 | 5.97 |

* Mole ratio of catalyst:B compound:Al compound = 1:20:1000

From the results of polymerization of Table 4, it may be confirmed that the catalyst activity is significantly changed due to the structure of the polymerization catalyst.

Specifically, when Complex 2 of Preparation Example 2 in which a methyl group and a phenyl group are introduced to a silyl group linking an indene substituted by a pyrrolidino group and a t-butylamido group is used as the polymerization catalyst, significantly higher catalyst activity was shown, as compared with Complex B of Comparative Preparation Example 2 having a structure in which a dimethyl group is substituted on a silyl group linking indene substituted by a pyrrolidino group and a t-butylamido group, and Complex C of Comparative Preparation Example 3 having a structure in which a diphenyl group is substituted on a silyl group linking indene substituted by a pyrrolidino group and a t-butylamido group.

In addition, when Complex 1 of Preparation Example 1 in which a methyl group and a phenyl group are introduced to a silyl group linking an indene substituted by a dimethylamino group and a t-butylamido group, and Complex 2 of Preparation Example 2 in which a methyl group and a phenyl group are introduced to a silyl group linking an indene substituted by a pyrrolidino group and a t-butylamido group are used as a polymerization catalyst, significantly higher catalyst activity was shown, as compared with Complex C of Comparative Preparation Example 4 in which a nitrogen-containing substituent is not introduced to indene.

That is, it was found that when a complex having a structure in which indene having a nitrogen-containing substituent introduced thereto and an amido group are linked by a silyl group substituted by an alkyl group and an aryl group is used as the polymerization catalyst, due to the unique characteristic represented by optimized three-dimensional/electrical properties of a silyl linking group substituted by an alkyl group and an aryl group, remarkably improved catalyst activity is shown as compared with the comparative complex.

Figure 4:
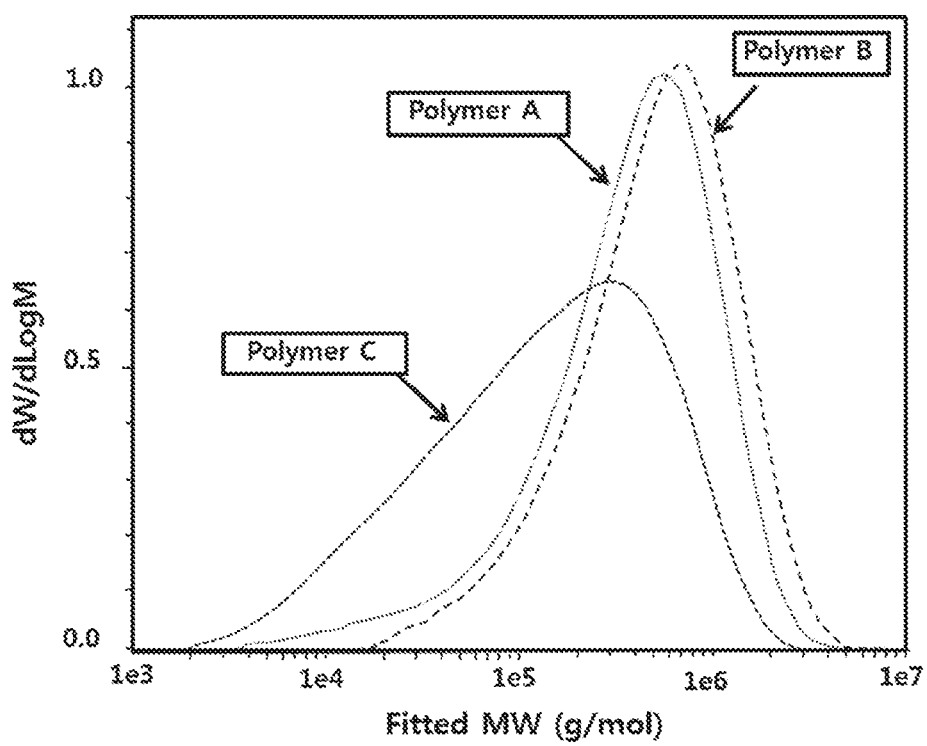
FIG. 4 is a GPC graph of the copolymers prepared in Comparative Examples 3, 4 and 6 [Polymer A: a polymer obtained using Complex A of Comparative Preparation Example 2 as a polymerization catalyst, that is, a polymer prepared in Comparative Example 3/Polymer B: a polymer obtained using Complex B of Comparative Preparation Example 3 as a polymerization catalyst, that is, a polymer prepared in Comparative Example 4/Polymer C: a polymer obtained using Complex C of Comparative Preparation Example 4 as a polymerization catalyst, that is, a polymer prepared in Comparative Example 6].

Meanwhile, a GPC graph of the high molecules prepared in Comparative Examples 3, 4 and 6 using a batchwise polymerization reactor is shown in FIG. 4, and a number average molecular weight (Mn), a weight average molecular weight (Mw), and a molecular weight distribution index (MWD) are described in the following Table 5:

TABLE 5

|  | Catalyst | Mn (×10$^{-3}$) | Mw (×10$^{-3}$) | MWD |
|---|---|---|---|---|
| Comparative Example 3 | Comparative Preparation Example 2 | 144 | 550 | 3.83 |
| Comparative Example 4 | Comparative Preparation Example 3 | 279 | 715 | 2.56 |
| Comparative Example 6 | Comparative Preparation Example 4 | 46 | 274 | 5.97 |

The polymers prepared using Complex A of Comparative Preparation Example 2 in which a dimethyl group is substituted on a silyl group linking indene substituted by a pyrrolidino group as a nitrogen-containing substituent and an amido group, and Complex B of Comparative Preparation Example 3 in which a diphenyl group is substituted on a silyl group linking indene substituted by a pyrrolidino group as a nitrogen-containing substituent and an amido group, as the polymerization catalyst represented a considerably narrow molecular weight distribution, despite their higher molecular weight, as compared with the polymer prepared using Complex C of Comparative Preparation Example 4 which is the diastereomer, as the polymerization catalyst.

From the results of GPC and TGIC as described above, it was found that the complex according to the present invention, the complex having a structure in which indene having a nitrogen-containing substituent introduced thereto and an amido group are linked by a silyl group substituted by an alkyl group and an aryl group may produce copolymers having a molecular weight distribution and a chemical composition distribution which are both narrow by adjusting the substituent, despite the presence of diastereomers, or may be applied to a diastereomer catalyst of high activity at high temperature which may produce copolymers having a narrow molecular weight distribution and a broad chemical composition distribution, which are useful for development of a new product.

Accordingly, the complex according to the present invention, the complex having a structure in which indene having a nitrogen-containing substituent introduced thereto and an amido group are linked by a silyl group substituted by an alkyl group or alkenyl group and an aryl group is easily prepared, has excellent catalyst activity at the time of polymerization at high temperature to reduce catalyst costs, and may easily produce copolymers having a narrow molecular weight distribution and a narrow composition distribution, and copolymers having a narrow molecular weight distribution and a broad chemical composition distribution, by simply changing the substituent, and thus, it may be said that the complex has a great commercial expectation effect.

As described above, though the Examples of the present invention have been described in detail, a person skilled in the art may make various variations of the present invention without departing from the spirit and the scope of the present invention, as defined in the claims which follow.

INDUSTRIAL APPLICABILITY

The transition metal complex according to the present invention or the catalyst composition including the transition metal complex has a high synthesis yield, may be easily prepared by an economical method, and also has excellent catalyst thermal stability to maintain high catalyst activity even at high temperature while having good copolymerization reactivity with other olefins, and may produce a high molecular weight polymer with a high yield, and thus, has high commercial practicality as compared with already known metallocene and non-metallocene-based single active site catalysts. The present inventors have developed catalysts which are diastereomer catalysts, but show a narrow molecular weight distribution characteristic like a single activity site catalyst, by controlling the ligands. That is, the copolymer prepared using the transition metal complex according to the present invention as a catalyst having high activity at high temperature has unique merits in that copolymers having a narrow molecular weight distribution and a narrow chemical composition distribution (CCD) may be easily prepared, and a product having a narrow molecular weight distribution and a broad chemical composition distribution (2 peaks) may be also prepared. Therefore, the transition metal catalyst composition according to the present invention may be useful for preparing an ethylene-based polymer selected from copolymers of ethylene and α-olefins having various physical properties.

The invention claimed is:

1. A compound represented by the following Chemical Formula Int-1:

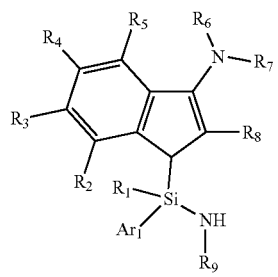

[Chemical Formula Int-1]

wherein $R_1$ is (C1-C20)alkyl or (C2-C20)alkenyl, in which the alkyl or alkenyl of $R_1$ may be further substituted by one or more substituents selected from the group consisting of halogen, (C6-C30)aryl and (C1-C20)alkyl(C6-C30)aryl;

$Ar_1$ is (C6-C30)aryl, in which the aryl of $Ar_1$ may be further substituted by one or more substituents selected from the group consisting of (C1-C20)alkyl, halo(C1-C20)alkyl and (C6-C30)aryl(C1-C20)alkyl;

$R_2$ to $R_5$ are each independently hydrogen, (C1-C20) alkyl, (C1-C20)alkoxy, halo(C1-C20)alkyl, (C3-C20) cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl or ((C1-C20)alkyl(C6-C30)aryl)(C1-C20)alkyl, or $R_2$ to $R_5$ are linked with an adjacent substituent to form a fused ring, in which the formed fused ring may be further substituted by one or more substituents selected from the group consisting of (C1-C20)alkyl, (C1-C20)alkoxy, halo(C1-C20)alkyl, (C3-C20)cycloalkyl, (C1-C20)alkyl(C6-C30)aryl, (C6-C30)aryl, (C6-C30)aryloxy, (C1-C20)alkyl(C6-C30) aryloxy, (C6-C30)aryl(C1-C20)alkyl and ((C1-C20)alkyl(C6-C30)aryl)(C1-C20)alkyl;

$R_9$ is (C1-C20)alkyl, (C3-C20)cycloalkyl or (C6-C30)aryl (C1-C20)alkyl;

$R_6$ and $R_7$ are each independently (C1-C20)alkyl, halo (C1-C20)alkyl, (C3-C20)cycloalkyl, (C6-C30)aryl, (C1-C20)alkyl(C6-C30)aryl, (C1-C20)alkoxy(C6-C30)aryl or (C6-C30)aryl(C1-C20)alkyl, or $R_6$ and $R_7$ are linked to each other to form a ring, in which the formed ring may be further substituted by one or more substituents selected from the group consisting of (C1-C20)alkyl, halo(C1-C20)alkyl, (C6-C30)aryl(C1-C20) alkyl, (C1-C20)alkoxy, (C3-C20)cycloalkyl, (C6-C20) aryl, (C1-C20)alkyl(C6-C30)aryl and (C6-C20) aryloxy; and $R_8$ is hydrogen or (C1-C20)alkyl.

2. A transition metal complex represented by the following Chemical Formula 1:

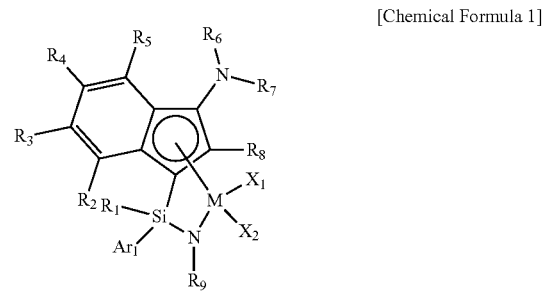

[Chemical Formula 1]

wherein

M is a Group 4 transition metal in the periodic table;

$R_1$ is (C1-C20)alkyl or (C2-C20)alkenyl, in which the alkyl or alkenyl of $R_1$ may be further substituted by one or more substituents selected from the group consisting of halogen, (C6-C30)aryl and (C1-C20)alkyl(C6-C30) aryl;

$Ar_1$ is (C6-C30)aryl, in which the aryl of $Ar_1$ may be further substituted by one or more substituents selected from the group consisting of (C1-C20)alkyl, halo(C1-C20)alkyl and (C6-C30)aryl(C1-C20)alkyl;

$R_2$ to $R_5$ are each independently hydrogen, (C1-C20) alkyl, (C1-C20)alkoxy, halo(C1-C20)alkyl, (C3-C20) cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl or ((C1-C20)alkyl(C6-C30)aryl)(C1-C20)alkyl, or $R_2$ to $R_5$ are linked with an adjacent substituent to form a fused ring, in which the formed fused ring may be further substituted by one or more substituents selected from the group consisting of (C1-C20)alkyl, (C1-C20)alkoxy, halo(C1-C20)alkyl, (C3-C20)cycloalkyl, (C1-C20)alkyl(C6-C30)aryl, (C6-C30)aryl, (C6-C30)aryloxy, (C1-C20)alkyl(C6-C30) aryloxy, (C6-C30)aryl(C1-C20)alkyl and ((C1-C20)alkyl(C6-C30)aryl)(C1-C20)alkyl;

$R_9$ is (C1-C20)alkyl, (C3-C20)cycloalkyl or (C6-C30)aryl (C1-C20)alkyl;

R₆ and R₇ are each independently (C1-C20)alkyl, halo(C1-C20)alkyl, (C3-C20)cycloalkyl, (C6-C30)aryl, (C1-C20)alkyl(C6-C30)aryl, (C1-C20)alkoxy(C6-C30)aryl or (C6-C30)aryl(C1-C20)alkyl, or R₆ and R₇ are linked to each other to form a ring, in which the formed ring may be further substituted by one or more substituents selected from the group consisting of (C1-C20)alkyl, halo(C1-C20)alkyl, (C6-C30)aryl(C1-C20)alkyl, (C1-C20)alkoxy, (C3-C20)cycloalkyl, (C6-C20)aryl, (C1-C20)alkyl(C6-C30)aryl and (C6-C20)aryloxy;

R₈ is hydrogen or (C1-C20)alkyl;

X₁ and X₂ are each independently halogen, (C1-C20)alkyl, (C2-C20)alkenyl, (C3-C20)cycloalkyl, (C6-C30)aryl, (C6-C30)ar(C1-C20)alkyl, ((C1-C20)alkyl(C6-C30)aryl)(C1-C20)alkyl, (C1-C20)alkoxy, (C6-C30)aryloxy, (C1-C20)alkyl(C6-C30)aryloxy, (C1-C20)alkoxy(C6-C30)aryloxy, $-OSiR^aR^bR^c$, $-SR^d$, $-NR^eR^f$, $-PR^gR^h$ or (C1-C20)alkylidene;

$R^a$ to $R^d$ are each independently (C1-C20)alkyl, (C6-C20)aryl, (C6-C20)ar(C1-C20)alkyl, (C1-C20)alkyl(C6-C20)aryl or (C3-C20)cycloalkyl; and $R^e$ to $R^h$ are each independently (C1-C20)alkyl, (C6-C20)aryl, (C6-C20)ar(C1-C20)alkyl, (C1-C20)alkyl(C6-C20)aryl, (C3-C20)cycloalkyl, tri(C1-C20)alkylsilyl or tri(C6-C20)arylsilyl;

with a proviso that when one of X₁ and X₂ is (C1-C20)alkylidene, the other one is ignored.

3. The transition metal complex of claim 2, wherein the transition metal complex is represented by the following Chemical Formula 2:

[Chemical Formula 2]

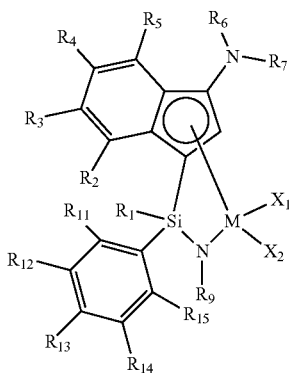

wherein

M, R₁, R₆, R₇, R₉, X₁ and X₂ are as defined in Chemical Formula 1 of claim 2;

R₂ to R₅ are each independently hydrogen, (C1-C20)alkyl, (C1-C20)alkoxy, halo(C1-C20)alkyl, (C3-C20)cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl or ((C1-C20)alkyl(C6-C30)aryl)(C1-C20)alkyl, or R₂ to R₅ are linked with an adjacent substituent by (C3-C7)alkylene, (C3-C7)alkenylene or (C4-C7)alkadienylene containing or not containing an aromatic ring to form a fused ring, in which the formed fused ring may be further substituted by one or more substituents selected from the group consisting of (C1-C20)alkyl, (C1-C20)alkoxy, halo(C1-C20)alkyl, (C3-C20)cycloalkyl, (C1-C20)alkyl(C6-C30)aryl, (C6-C30)aryl, (C6-C30)aryloxy, (C1-C20)alkyl(C6-C30)aryloxy, (C6-C30)aryl(C1-C20)alkyl and ((C1-C20)alkyl(C6-C30)aryl)(C1-C20)alkyl; and R₁₁ to R₁₅ are each independently hydrogen, (C1-C20)alkyl, halo(C1-C20)alkyl or (C6-C30)aryl(C1-C20)alkyl.

4. The transition metal complex of claim 3, wherein R₆ and R₇ are each independently (C1-C20)alkyl, (C3-C20)cycloalkyl or (C6-C30)aryl, or R₆ and R₇ are linked by (C3-C7)alkylene containing or not containing an aromatic ring to form a ring, in which the formed ring may be further substituted by one or more substituents selected from the group consisting of (C1-C20)alkyl, (C6-C30)aryl(C1-C20)alkyl, (C1-C20)alkoxy, (C3-C20)cycloalkyl, (C6-C20)aryl, (C1-C20)alkyl(C6-C30)aryl and (C6-C20)aryloxy.

5. The transition metal complex of claim 3, wherein

M is tetravalent titanium, zirconium or hafnium;

R₁ is (C1-C20)alkyl;

R₁₁ to R₁₅ are each independently hydrogen or (C1-C20)alkyl;

R₃ to R₅ are each independently hydrogen or (C1-C20)alkyl, or R₃ to R₅ are linked with an adjacent substituent by

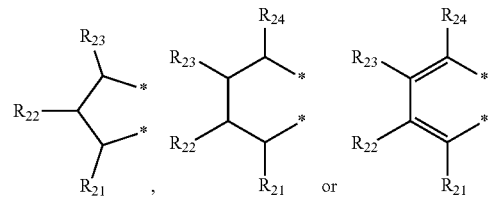

to form a fused ring;

R₂₁ to R₂₄ are each independently hydrogen or (C1-C20)alkyl;

R₆ and R₇ are each independently (C1-C20)alkyl, or R₆ and R₇ are linked by

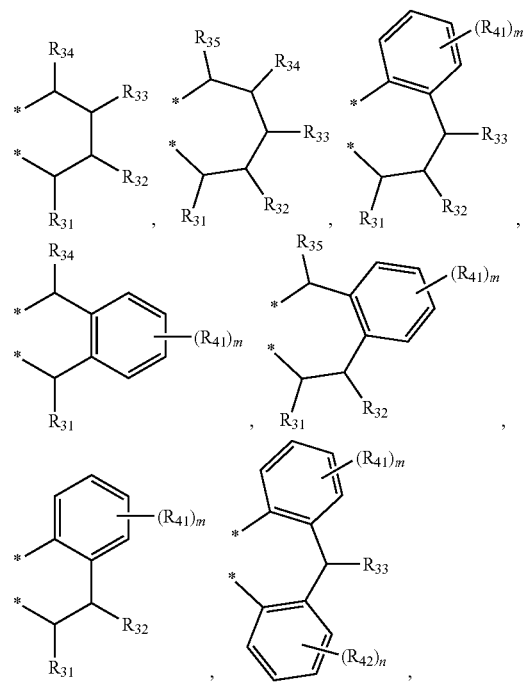

-continued

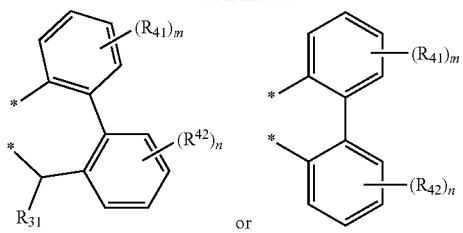

to form a ring;

R_{31} to R_{35}, R_{41} and R_{42} are each independently hydrogen or (C1-C20)alkyl;

m and n are each independently an integer of 1 to 4;

$R_9$ is (C1-C20)alkyl or (C3-C20)cycloalkyl;

$X_1$ and $X_2$ are each independently halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C1-C20)alkyl(C6-C30)aryloxy, —OSiR$^a$R$^b$R$^c$, —SR$^d$, —NR$^e$R$^f$ or —PR$^g$R$^h$; and R$^a$ to R$^h$ are each independently (C1-C20)alkyl or (C6-C20)aryl.

6. The transition metal complex of claim 2, wherein the transition metal complex is selected from the following compounds:

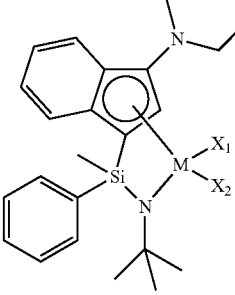

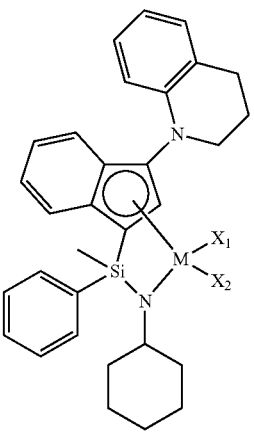

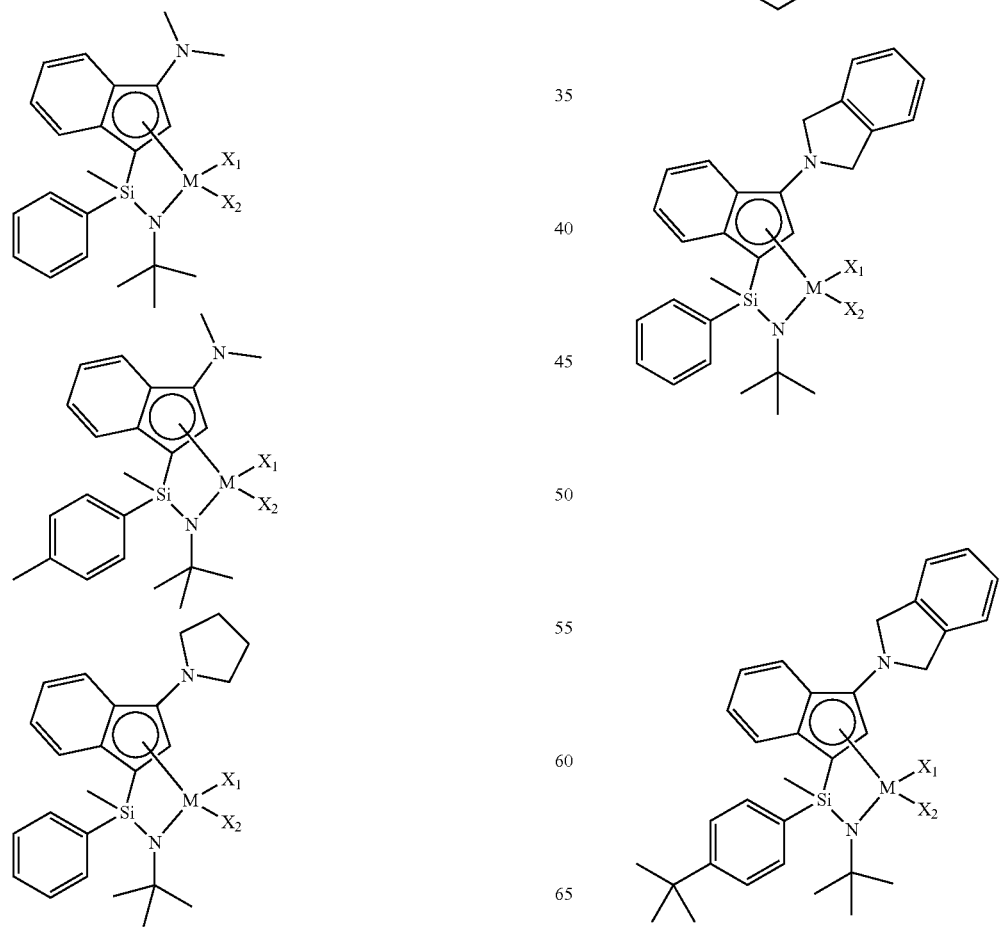

-continued

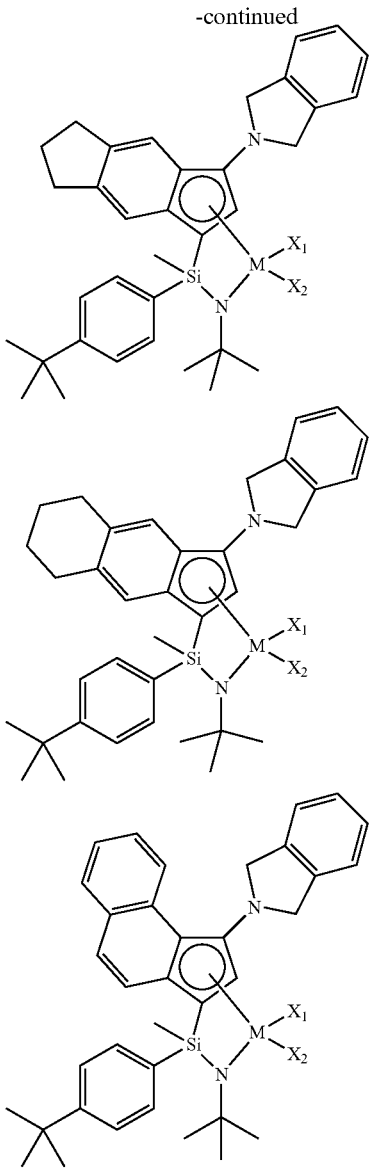

wherein

M is tetravalent titanium, zirconium or hafnium;

$X_1$ and $X_2$ are each independently halogen, (C1-C20)alkyl, (C3-C20)cycloalkyl, (C6-C30)aryl, (C6-C30)ar(C1-C20)alkyl, (C1-C20)alkoxy, (C6-C30)aryloxy, (C1-C20)alkyl(C6-C30)aryloxy, —OSi$R^aR^bR^c$, —S$R^d$, —N$R^eR^f$ or —P$R^gR^h$; and $R^a$ to $R^h$ may be each independently (C1-C20)alkyl or (C6-C20)aryl.

7. The transition metal complex of claim 2, for use in preparing a copolymer of ethylene and an α-olefin having a unimodal GPC graph.

8. A transition metal catalyst composition for preparing an ethylene homopolymer or a copolymer of ethylene and an α-olefin, comprising:

the transition metal complex of claim 2; and
a cocatalyst selected from the group consisting of an aluminum compound, a boron compound or a mixture thereof.

9. The transition metal catalyst composition of claim 8, wherein
the aluminum compound is one or a mixture of two or more selected from the group consisting of alkylaluminoxane and organic aluminum, which is one selected from the group consisting of methylaluminoxane, modified methylaluminoxane, tetraisobutylaluminoxane, trimethylaluminum, triethylaluminum and triisobutylaluminum, or a mixture thereof; and
the boron compound is one selected from the group consisting of tris(pentafluorophenyl)borane, N,N-dimethylanilinium tetrakis(pentafluorophenyl)borate, N,N-ditetradecylanilinium tetrakis(pentafluorophenyl)borate, N,N-dihexadecylanilinium tetrakis(pentafluorophenyl)borate, N,N-dioctadecylanilinium tetrakis(pentafluorophenyl)borate and triphenylmethylinium tetrakis(pentafluorophenyl)borate, or a mixture thereof.

10. The transition metal catalyst composition of claim 8, wherein a ratio of the transition metal complex and the cocatalyst is in a range of 1:1 to 2,000, as a mole ratio of the transition metal (M):the aluminum atom (Al).

11. The transition metal catalyst composition of claim 8, wherein a ratio of the transition metal complex and the cocatalyst is in a range of 1:0.1 to 100:1 to 2,000, as a mole ratio of the transition metal (M):the boron atom (B):the aluminum atom (Al).

12. A copolymerization method for copolymerizing ethylene, propylene and optionally a non-conjugated diene, using the transition metal complex of claim 2 as a catalyst.

13. A method for preparing a copolymer of ethylene and an α-olefin having a chemical composition distribution represented by a unimodal graph, using the transition metal complex of claim 7.

14. A method for preparing a copolymer of ethylene and an α-olefin having a chemical composition distribution represented by a bimodal graph, using the transition metal complex of claim 7.

15. A method for preparing an ethylene homopolymer or a copolymer of ethylene and an α-olefin, using the transition metal catalyst composition of claim 8.

16. The method of claim 15, wherein a comonomer polymerized with the ethylene is one or a mixture of two or more selected from the group consisting of propylene, 1-butene, 1-pentene, 1-hexene, 1-heptene, 1-octene, 1-decene, 1-undecene, 1-dodecene, 1-tetradecene, 1-hexadecene, 1-itocene, 3-butadiene, 1,4-pentadiene, 2-methyl-1,3-butadiene, cyclopentene, cyclohexene, cyclopentadiene, cyclohexadiene, norbornene, 5-vinylidene-2-norbornene (VNB), 5-methylene-2-norbornene (MNB), 5-ethylidene-2-norbornene (ENB) and styrene, and an ethylene content in the copolymer of ethylene and an α-olefin is 30 to 99 wt %.

17. The method of claim 15, wherein a pressure in a reactor for homopolymerization of ethylene or copolymerization of ethylene and an α-olefin is 6 to 150 atm, and polymerization reaction temperature is 50 to 200° C.

18. A copolymerization method for copolymerizing ethylene, propylene and optionally a non-conjugated diene, using the catalyst composition including a transition metal complex of claim 8.

\* \* \* \* \*